US006780414B2

(12) United States Patent
Maurelli et al.

(10) Patent No.: US 6,780,414 B2
(45) Date of Patent: *Aug. 24, 2004

(54) METHODS OF IDENTIFYING BACTERIAL GENES THAT ARE INCOMPATIBLE WITH BACTERIAL PATHOGENICITY, AND THE USE OF SUCH GENES, SUCH AS CADA, TO REDUCE PATHOGENICITY IN A BACTERIA OR TO COMBAT PATHOGENIC BACTERIAL INFECTIONS

(75) Inventors: Anthony T. Maurelli, Silver Spring, MD (US); Reinaldo E. Fernández, Silver Spring, MD (US); Craig A. Bloch, Ann Arbor, MI (US); Alessio Fasano, West Friendship, MD (US)

(73) Assignees: Henry M. Jackson Foundation for the Advancement of Military Medicine, Inc., Rockville, MD (US); The University of Maryland, Baltimore, Baltimore, MD (US); The Regents of the University of Michigan, Ann Arbor, MI (US)

( * ) Notice: Subject to any disclaimer, the term of this patent is extended or adjusted under 35 U.S.C. 154(b) by 12 days.

This patent is subject to a terminal disclaimer.

(21) Appl. No.: 10/034,213
(22) Filed: Jan. 3, 2002

(65) Prior Publication Data

US 2002/0192225 A1 Dec. 19, 2002

Related U.S. Application Data

(62) Division of application No. 09/281,274, filed on Mar. 30, 1999, now Pat. No. 6,344,201.
(60) Provisional application No. 60/080,202, filed on Mar. 31, 1998.

(51) Int. Cl.$^7$ ............................................... A61K 39/00

(52) U.S. Cl. ................................ 424/184.1; 424/234.1; 424/241.1; 514/250

(58) Field of Search ....................... 514/250; 424/184.1, 424/234.1, 241.1

(56) References Cited

U.S. PATENT DOCUMENTS 5,502,055 A * 3/1996 Wang

FOREIGN PATENT DOCUMENTS

| FR | 3795 | 12/1965 |
|---|---|---|
| WO | WO 85/03521 | 8/1985 |
| WO | 0 279 273 A2 | 8/1988 |
| WO | WO 95/15396 | 6/1995 |

OTHER PUBLICATIONS

Yolanda et al. J.Food Science. 1997. 62(4), p. 870, abstract only.*
Ordonez et al. J.Food Protection. 1997. 60(11): p. 1371, abstract only.*
Gabastou et al. Phatologie Biolgie. 1996. 44(4), p. 275, abstract only.*
Keusch et al. Biochem. Biophys. Res. Comm. 1984. 121(1): 69–76.*
Dela Vega et al. The Euro Journal. 1995. 14(23): 6059–65.*
Dela Vega. et al. J.Bacteriol. July 1996. 178(13): 3714–3721.*
Zaleski et al. Int. J. Biochem. 1980, 11(3–4): 237–242. Abstract only.*
MacDonald et al. Biochim Biophys Acta. 1981. 663(1): 302–313. Abstract only.*
J.M. Gabastou et al., "Amines Digestives D'Origine Bacterienne et Troubles Comportementaux, A Propos d'une Observation," *Path. Biol.* 44(4): (1996)., abstract only. no translation.
A.I. Ordoñez et al., "Formation of Biogenic Amines in Idiazabal Ewe's–Milk Cheese: Effect of Ripening, Pasteurization, and Starter," *J. Food. Protection* 60(11): 1371–5 (1997).
Y. Sanz & F. Toldrá, "Polyamines Affect Activity of Aminopeptidases from *Lactobacillus sake,*" *J. Food Science* 62(4): 870–2 (1997).
Zaleski et al., *Int. J. Biochem.* 11(3–4): 237–42 (Abstract only) (1980).
MacDonald et al., *Biochim. Biophys. Acta.* 663(1): 302–13 (Abstract only) (1981).

(List continued on next page.)

Primary Examiner—Jennifer E. Graser
(74) Attorney, Agent, or Firm—Finnegan, Henderson, Farabow, Garrett & Dunner, L.L.P.

(57) ABSTRACT

"Black holes" in the genomes of bacterial pathogens represent deletions of "anti-virulence" genes, i.e. genes that are detrimental to a pathogenic lifestyle. Identification of the missing genetic loci in the "black hole" identifies genes that are incompatible with the bacteria's pathogenicity. These genes, their gene products, and compounds generated by the enzymatic action of these gene products represent potential new compounds that are inhibitory to the bacterial pathogen and thus useful as pharmaceuticals. The utility of this concept is demonstrated in the missing gene for lysine decarboxylase, and the resulting inhibitory activity of cadaverine (the diaminoalkyl reaction product of lysine decarboxylase) on the Shigella enterotoxins. Diaminoalkyl compounds are therefore potent inhibitors of *E. coli* and Shigella spp. enterotoxins. Lysine decarboxylase generated from the gene cadA results in attenuation of the enterotoxic effects. New methods of use of diaminoalkyl compounds as medicaments are described. New uses of genetic constructs containing a cadA sequence, or other "anti-virulence" gene, for biochemical probes, for toxin receptor identification, and for pharmaceutical discovery are described. Additional uses are described for vaccines and DNA vaccine delivery.

5 Claims, 5 Drawing Sheets

OTHER PUBLICATIONS

B.A. McCormick et al. "Inhibition of *Shigella flexneri*–induced transepithelial migration of polymorphonuclear leucocytes by cadaverine," *Cellular Microbiology*, 1(2): 143–155 (1999).

A.L. Dela Vega & A.H. Delcour, "Cadaverine induces closing of *E. coli* porins," *The EMBO Journal*, 14(23): 6058–65 (1995).

R. Iyer & A.H. Detcour, "Complex Inhibition of OmpF and OmpC Bacterial Porins by Polyamines," *Journal of Biological Chemistry*, 272(30): 18595–18601 (1997).

R. Flachmann et al., "Molecular biology of pyridine nucleotide biosynthesis in *Escherichia coli*, Cloning and characterization of quinolinate synthesis genes nadA and nadB," *Eur J. Biochem*, 175(2): 221–8 (1998).

S.B. Formal et al., "Shigella Vaccines," *Reviews of Infectious Diseases*, vol. 11, Supplement 3, pp. S547–S551 (1989).

S.B. Formal et al. "Protection of Monkeys Against Experimental Shigellosis with a Living Attenuated Oral Polyvalent Dysentery Vaccine," *Journal of Bacteriology*, 92(1): 17–22 (.1966).

S.B. Formal et al., "Attenuation of Strains of Dysentery Bacilli," *International Symposium on Enterobacterial Vaccines, Berne 1968, Symp. Series Immunobiol.* Standard., 15: 73–78 (1971).

J. Hacker et al., "Pathogenicity islands of virulent bacteria: structure, function and impact on microbial evolution," *Molecular Microbiology*, 23(6): 1089–1097 (1997).

G.T. Keusch & M. Jacewicz, "Primary Amines and Chloroquine Inhibit Cytotoxic Responses to Shigella Toxin and Permit Late Antibody Rescue of Toxin Treated Cells," *Biochemical and Biophysical Research Communications*, 121(1): 69–76 (1984).

J.E. Leach & F.F. White, "Bacterial Avirulence Genes," *Annu. Rev. of Phytopathol.*, 34: 153–179 (1996).

N. Nakata et al. "The absence of a surface protease, OmpT, determines the intercellular spreading ability of Shigella; the relationship between the *ompT* and *kcpA* Ioci," *Molecular Microbiology*, 9(3): 459–468 (1993).

P.J. Sansonetti et al., "Alterations in the Pathogenicity of *Escherichia coli* K–12 After Transfer of Plasmid and Chromosomal Genes from *Shigella flexneri*," *Infection and Immunity*, 39(3): 1392–1402 (1983).

English abstract No. 07602005 for European Patent Office Patent No. 0 279 273 A2.

International Search Report dated Oct. 6, 1999.

A.T. Maurelli et al., "'Black holes' and bacterial pathogencity: A large genomic delation that enhances the virulence of Shigella spp. and enteroinvasive *Escherichia coli,*" *Proc. Natl. Acad. Sci. USA*, 95:3943–3948 (1998).

\* cited by examiner

US 6,780,414 B2

METHODS OF IDENTIFYING BACTERIAL GENES THAT ARE INCOMPATIBLE WITH BACTERIAL PATHOGENICITY, AND THE USE OF SUCH GENES, SUCH AS CADA, TO REDUCE PATHOGENICITY IN A BACTERIA OR TO COMBAT PATHOGENIC BACTERIAL INFECTIONS

CROSS-REFERENCE TO RELATED APPLICATION

This is a division of application Ser. No. 09/281,274, filed Mar. 30, 1999, now U.S. Pat. No. 6,344,201, and claims the benefit of U.S. provisional application No. 60/080,202, filed Mar. 31, 1998, both of which are incorporated herein by reference.

GOVERNMENT INTEREST

The invention described herein may be manufactured, licensed, and used for governmental purposes without payment of royalties to us thereon.

FIELD OF THE INVENTION

This invention relates to the inventive procedure for identifying "anti-virulence" genes which are incompatible with virulence. This inventive principle is illustrated by the identification of the anti-virulence gene cadA. A further aspect of this invention is derived from this identification, because the gene products of these anti-virulence genes, or the compounds generated enzymatically by these gene products, are useful as pharmaceuticals. As exemplified by the compound generated by the product of the cadA gene (lysine decarboxylase), the invention relates to the use as a pharmaceutical of the diaminoalkanes and polyaminoalkanes in the treatment and prevention of pathogenic bacterial infections. Of particular use is cadaverine (1,5-diaminopentane).

As further support, and as a further embodiment, is the identification of nadA and nadB as anti-virulence genes, and the pharmaceutical use of the corresponding enzymatically generated compound, quinolinate.

The identification of a gene related to non-pathogenicity also permits the modification of pathogenic bacteria with the gene to thereby diminish pathogenicity. Thus, the invention includes modified pathogenic bacteria, including DNA constructs, vectors, plasmids, and organisms. This aspect of the invention permits the generation of vaccines that could protect against Shigella and other pathogenic bacteria such as enteroinvasive bacteria. The invention also encompasses delivery of DNA vaccines, where a gene of interest, or a fragment thereof, is delivered via these attenuated bacteria to the digestive epithelia without inducing diarrhea.

The invention further relates to an assay for pathogenicity by probing for cadA gene deletion in bacterial samples or cultures of unknown pathogenicity. Alternatively, pathogenicity may be determined by assaying for lysine decarboxylase activity as the protein product of this gene. The invention includes DNA constructs, fragments, vectors, plasmids and antibodies useful for constructing such pathogenicity assays.

BACKGROUND OF THE INVENTION

Mankind exists in conjunction with a world of microorganisms whose number far outnumbers man's. Some microorganisms are friendly co-habitants such as *Escherichia coli*, while others such as Shigella cause such dangerous maladies as bloody diarrhea (hemorrhagic colitis), hemolytic uremic syndrome, and dysentery.

Bacteria of the genus Shigella are gram negative enteric pathogens which are the causative agents of bacillary dysentery or shigellosis. Shigella infection accounts for a considerable fraction of acute diarrheal diseases worldwide and is an important public health problem in developing countries where bacillary dysentery remains a major cause of childhood mortality. The worldwide incidence of bacillary dysentery is estimated to exceed 200 million cases annually. About 5 million cases require hospitalization and about 650,000 persons die of shigellosis each year (Institute of Medicine (1986) The prospect for immunizing against Shigella spp., p. 329–337. In: *New Vaccine Development: Establishing priorities*. Vol. 2 Diseases of importance in developing countries. National Academy Press, Washington, D.C.). Shigellosis continues to be an important public health concern even in the United States with over 32,000 cases reported in 1995 (Centers for Disease Control and Prevention. 1995. Summary of notifiable diseases, United States, 1995. *MMWR* 44:1–3.). Of principal importance are foodborne outbreaks and outbreaks in institutional settings (day care centers, nursing homes, etc.) and on Indian reservations. The clinical presentation of shigellosis can range from a mild diarrhea to severe dysentery with frequent passage of bloody, mucoid, small volume stools. The disease is characterized by extensive damage to the colonic epithelial layer, cell death, ulceration and inflammation of the colon. While infections are usually self-limiting and do not spread from the lamina propria to the submucosa, shigellosis can be life-threatening in young or malnourished patients (DuPont, H. L. 1995. Shigella species (Bacillary dysentery), p. 2033–2039. In G. L. Mandell, et al. (eds.), *Principles and Practice of Infectious Diseases*. Churchhill Livingstone Inc., New York, N.Y.).

The primary means of human to human transmission of Shigella is by the fecal-oral route. Most cases of shigellosis are caused by the ingestion of fecally-contaminated food or water. In the case of foods, the major factor for contamination is the poor personal hygiene of food handlers. The low infectious dose of Shigella spp. presents a challenging problem. Volunteer studies showed that the $ID_{50}$ (the infectious dose required to cause disease in 50% of the volunteers) of Shigella is as low as 200 shigellae although it has been reported that the ingestion of as few as 10 organisms is sufficient to cause disease (DuPont. H. L., et al. (1989) *J. Infect Dis.* 159:1126–1128). The low $ID_{50}$ of Shigella accounts for its high communicability, particularly in impoverished and crowded populations. One consequence of this feature is that a contaminated food source has the potential to cause explosive outbreaks of dysentery with secondary cases likely to occur among close contacts of infected individuals. Thus, infected food handlers can contaminate food and spread infection among large numbers of individuals.

Maurelli and Lampel describe several examples of foodborne outbreaks of shigellosis (Maurelli and Lampel (1997) Shigella species, p. 216–227. In M. P. Doyle, et al. (eds.), Food Microbiology: Fundamentals and Frontiers. American Society for Microbiology Press, Washington, D.C.). Daycare workers and children attending day care facilities are placed at risk when a child infected with Shigella is present. The bacteria are shed in feces and the immature personal hygiene habits of very young children can easily lead to infection of other children as well as care providers (Mohle-Boetani, J. C., et al. (1995) *Am. J. Pub. Health* 85:812–816). With a low infectious dose required to cause disease coupled with oral transmission via fecally-contaminated food and water, it is not surprising that dysentery caused by Shigella spp. follows in the wake of many natural (earthquakes, floods, famine) and man-made disasters (war). Civil wars in Burundi and Rwanda led to massive movement of refugees. An outbreak of dysentery in a refugee camp in Rwanda in late 1993 affected more than 6,000 people (attack rate>32%), mostly children under five years old (Paquet, C., et al. (1995) Une epidemie de dysenteriae à Shigella dysenteriae type 1 dans un camp de refugies au Rwanda, Sauté 5:181–184). In August, 1994, more than 15,500 cases of bloody diarrhea were reported from three refugee camps in Zaire (Centers for Disease Control and Prevention. (1996) Morbidity and mortality surveillance in Rwandan refugees—Burundi and Zaire, 1994. *MMWR* 45:104–107). All of these factors are exacerbated by the fact that shigellae are becoming increasingly resistant to most antimicrobial agents commonly used in the treatment of diarrheal diseases (Centers for Disease Control and Prevention. (1994) Addressing emerging infectious disease threats: A prevention strategy for the United States. U.S. Department of Health and Human Services, Public Health Service, Atlanta, Ga.).

There exists no effective vaccine against shigellosis. Previous attempts to develop a vaccine against enteropathogenic bacteria have suffered from a failure to engender immunogenicity without also generating diarrhea, or from requiring multiple doses as well as boosters of high numbers of viable bacteria. Thus, there is an unsatisfied need in the art for a vaccine against shigellosis. Such a vaccine may be a bacteria which is enteroinvasive and thereby capable of delivering an immunogen to a host, but which is not reactogenic or diarrheic in the host (Sizemore, D. R., et al. (1995) *Science* 270:299–302).

Shigella are also interesting in that they share significant homology with *E. coli*, a generally benign bacteria. Indeed, the four species of Shigella are so closely related to *E. coli* that all of these bacteria could be considered members of a single species. They share greater than 90% homology by DNA—DNA reassociation analysis (Brenner, D. J., et al. (1969) *J. Bacteriol.* 98, 637–650) and display colinearity of their chromosomes such that gene transfer by conjugation and transduction and formation of recombinants between Shigella and *E. coli* occur with high efficiency (Formal, S. B., et al. (1970) *Infect. Immun.*, 1, 179–287). Nevertheless, Shigella spp. are serious pathogens that cause bacillary dysentery, whereas *E. coli* (with the exception of certain pathogenic clones) are commensals of the human intestine.

Given the similarity between pathogens, such as the toxic Shigella, and commensals, such as the benign *E. coli*, there exists a need in the art for a simple and reliable test to distinguish between these closely related microorganisms. In addition, there exists a need for probes to identify receptors associated with these bacteria and their toxins for the ultimate goal of providing information on the evolutionary basis of pathogenicity. Knowledge of receptor characteristics would facilitate rational vaccine design wherein the naturally invasive nature of these bacteria may be exploited in positive ways. Furthermore, because of the severity and widespread nature of pathogenic bacterial infections, there exists a need in the art for a rational approach to this analysis of virulence and pathogenesis, and also for a rational approach to the discovery of new pharmaceuticals for treatment of pathogenic bacterial infections.

Thus, there is a need in the art for an effective method of preventing or treating diseases caused by pathogenic organisms such as Shigella as well as ways of distinguishing such pathogenic organisms from nonpathogenic organisms.

SUMMARY OF THE INVENTION

The present invention satisfies these needs by describing the correlation between pathogenicity and a known gene, cad, which produces the enzyme lysine decarboxylase (LDC) and the applications of this correlation. In many wild-type bacteria, presence of this gene is correlated with lack of pathogenicity. Based on this observation, we have identified a new inhibitor of the enterotoxins produced by pathogenic bacteria: the enzymatically generated product of LDC—cadaverine. Cadaverine is a diaminoalkyl compound, only one of a large related class of such compounds, which provides promising therapeutics for the treatment and prevention of pathogenic bacterial infections. Additionally, we have discovered that expression of this gene is correlated only with decreased diarrheic ability, while retaining invasive action, an effect which is invaluable for designing DNA vaccine delivery vehicles and vaccines against enteroinvasive bacteria.

This discovery marks an important step in the rational analysis of virulence, and in the rational search for new treatment strategies and pharmaceuticals. Although the evolution of bacterial pathogens from non-pathogenic ancestors has been thought to proceed through the acquisition of virulence genes, we have discovered that the loss of "antivirulence" genes causes genomic black holes and results in a pathogenic phenotype.

This discovery enables the discovery of new pharmaceuticals by merely comparing the genomes of a pair of closely related virulent/avirulent species, identifying missing "antivirulence" genes in the virulent strain, and testing the product(s) of this missing gene (both the protein, and any enzymatically generated compounds) for inhibitory effects on the invasive bacteria, or prophylactic effects on the disease condition. This approach has been successfully demonstrated for *Shigella flexneri*, where the "antivirulence" gene is cadA, and the new pharmaceutical is cadaverine, but it is equally applicable to other pathogenic bacteria. Initial results also have identified two more antivirulence genes, nadA and nadB, and their corresponding enzymatically produced compound, quinolinate.

DETAILED DESCRIPTION OF THE INVENTION

Figure 1:
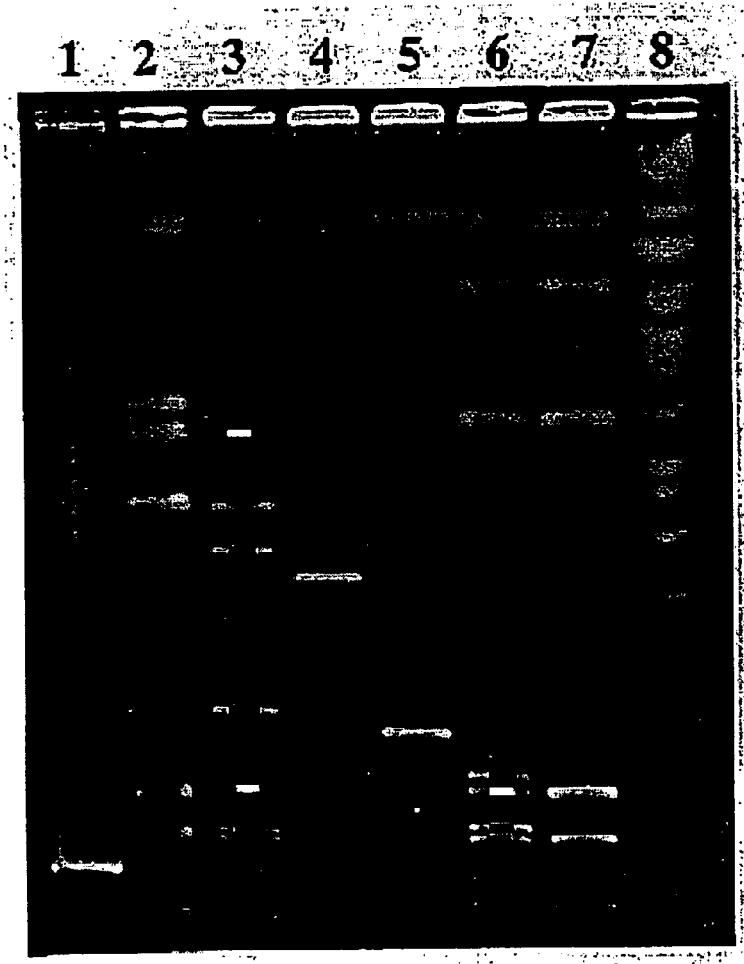
FIG. 1 shows the pulsed-field gel electrophoresis separation of genomic segments, illustrating transduction fidelity and genetic map conservation as described in the Examples.

The present invention relates to identifying compositions for treating or preventing disease or disorders caused by pathogenic bacteria, as well as identifying such pathogenic bacteria. By pathogenic bacteria, we mean bacterial microorganisms which cause disease in an animal host such as a human or other mammal or livestock such as chickens and pigs. Examples of bacterial pathogens are the four species of Shigella, enteroinvasive *Escherichia coli* (EIEC), Yersinia, Salmonella, Mycobacterium, Legionella, Listeria, and enterohemorrhagic *E. coli* (EHEC), among others. Some new strains of pathogenic *E. coli* have been discovered, so the need to identify pathogens remains significant.

We have discovered that pathogenic bacteria can be distinguished from nonpathogenic bacteria based on the absence of a gene or genetic loci. We have focused our initial efforts on Shigella, a genus of pathogenic bacteria that includes four species of Shigella, all of which cause bacillary dysentery, also known as shigellosis. Specifically, we considered the gene cadA which encodes the enzyme lysine decarboxylase (LDC) which, in turn, decarboxylates lysine to form a diaminoalkane known as cadaverine (1,5-diaminopentane) and $CO_2$.

In addition to cadA and its product LDC, the invention also relates to other genetic loci that include amino acid decarboxylase genes. Included among these are genes encoding lysine decarboxylase of *Hafnia alvei* (GenBank accession no. X03774) and ornithine decarboxylase (speC, which decarboxylates ornithine to produce the diaminoalkane putrescine, GenBank accession no. M33766) of *E. coli* K12, both of which share significant sequence similarity with cadA from either *E. coli* K12 or *Salmonella typhimurium* (GenBank M76411 and U37109, respectively). This invention also includes the gene designated ldc (Kikuchi, Y., et al. (1997) *J. Bacteriol.* 179, 4486–4492), that constituently expresses a less reactive LDC that also decarboxylates lysine to form cadaverine. Based on these activity profiles, the invention also includes the gene encoding arginine decarboxylase, which produces agmatine, a diamino derivative of arginine.

In assessing cadA and LDC, we compared the production of LDC between the four toxic Shigella species, the closely related and benign *E. coli* and the few known pathogenic *E. coli* clones, particularly the enteroinvasive *E. coli* (EIEC) that resembles a genetic hybrid between *E. coli* and Shigella (Example 1, A and Table 1). As set forth below in Example 3 and Table 2, we confirmed the almost universal observation of expression of LDC activity by strains of *E. coli*, and the absence of LDC expression in the pathogenic Shigella spp. and EIEC. These data suggested to us that expression of LDC from cadA might be incompatible with virulence and genomic deletions might account for pathogenicity.

To test this hypothesis, we transformed a wild-type strain of *S. flexneri* 2a with a cloned copy of cadA to form BS529. As set forth in Example 4 and Table 2 below, we found that the transformed *S. flexneri* 2a BS529 expressed LDC and that such expression attenuated the toxic effect as studied in rabbit ileal loops (Example 5), in Ussing chambers (Example 6), and in the polymorphonuclear leukocyte (PMN) transepithelial migration assay (Example 8). These three assays are known and accepted virulence assays. The rabbit ileal loop assay measures fluid volume as an indication of the intestinal response to enterotoxins. The Ussing chamber measures transepithelial (ileum) changes in resistivity and in electrical potential which are an indication of $Cl^-$ secretion and thus, like the ileal loop assay, indicate a diarrheic effect. The PMN assay measures the movement of PMN cells into a model epithelial cell layer in response to an invasive bacteria. This in vitro tissue culture assay models the in vivo inflammation process which heralds the onset of bacterial infection. As described in detail in Example 8, the PMN cells are attracted to the site of bacterial invasion in preparation for ingesting and destroying the invading bacteria, yet expression of cadA by Shigella abolished the transepithelial signaling of PMN normally induced by Shigella.

Based on the above virulence assays, we further examined the inhibitory effect of LDC expression. BS529 supernatants were applied to supernatants from LDC-strains, as also set forth in Example 5. We found that a factor in the BS529 supernatant inhibits the enterotoxin activity of the $LDC^-$ strains.

To identify this factor, we analyzed the BS529 supernatant for cadaverine, the product of LDC, as set forth in Example 7, and determined that the supernatant contained levels of cadaverine similar to those produced by nonpathogenic bacteria under inducing conditions. To confirm cadaverine's effect, we added cadaverine to the supernatant of wild-type *S. flexneri* and found that it also inhibited enterotoxin activity in the Ussing chamber, but that cadaverine alone did not change tissue resistance. See Example 7 and Table 3.

In assessing the mechanism of action of cadaverine, we noted that *S. flexneri* produces at least two enterotoxins, known as ShET1 and ShET2, which are believed to act via different pathways. As set forth in Example 7, pretreatment of rabbit mucosa with cadaverine protected the mucosa from the effect of the enterotoxins added after cadaverine was removed in the Ussing chamber assay. Cadaverine's protective ability suggests that cadaverine functions by acting directly on the target cell, attenuating the effect of pathogenic bacterial enterotoxins.

Among the physiological actions that may be responsible for cadaverine activity are closing ion channels induced by bacterial toxins, altering intracellular signaling or displacing toxin on cellular receptors. Of course, we do not intend to be limited by this list of possible physiological actions or by our present belief that cadaverine acts directly on the target cell.

These studies demonstrate that cadaverine, a diaminoalkane, can protect target cells from enterotoxins produced by pathogenic bacteria such as Shigella and EIEC. Additional studies on cadaverine demonstrate its potent inhibitory activity against other bacterial toxins. As set forth in Tables 4 and 5, cadaverine exhibits virulence inhibiting activity against *Campylobacter jejuni, Shigella dysenteriae* 1, *Yersinia enterocolitica*, and *Bacteroides fragilis*. Table 5 also demonstrates a strong correlation between the absence of LDC activity in a bacterial pathogen and the ability of cadaverine to inhibit toxin(s) produced by that pathogen. This correlation can serve as a predictor of which bacterial pathogens and their toxins will be inhibited by cadaverine or other diaminoalkanes.

Thus, the invention relates to a pharmaceutical composition comprising an amount of a diaminoalkane sufficient to protect target cells from enterotoxins produced by a variety of pathogenic bacteria, together with a pharmaceutically acceptable carrier. Although cadaverine is the preferred diaminoalkane, other diaminoalkanes are within the scope of the invention. Similarly, although Shigella is the pathogenic bacteria of one preferred embodiment, the invention includes other such bacteria.

As would be recognized by one of ordinary skill in the art, diaminoalkanes encompass any compound of the general structure $NH_2—(CH_2)_n—NH_2$, where n may be an integer from 2 to 12, and any structural isomers thereof (i.e. 1,5-; 1,4-; 1,3-diaminopentane, etc.). Other products of decarboxylase enzymes would also be included, for example, the diamine, agmatine, which is generated by arginine decarboxylase. Additionally, the invention encompasses the salts of the diaminoalkanes, including but not limited to, for example, dihydrochloride salts. Cadaverine (1,5-diaminopentane, n=5) is a preferred embodiment and putrescine (1,4-diaminobutane, n=4) is another.

Diaminoalkanes, though known in the art, are novel in their uses as medicaments for the treatment or prevention of enteropathogenic diseases such as dysentery and hemorrhagic colitis. They may also be bound to other molecules, such as proteins, or radioactive probes, for uses as diagnostic reagents and the study of bacterial pathogen evolution. In addition, the compounds of the invention may be modified using techniques that are standard in the art to, for example, increase bioavailability, increase the half life, or for other purposes well known in the art.

Another embodiment of the invention relates to polymeric amines with enterotoxin inhibition properties. This is of use, for example, in vaccines containing enterotoxin producing bacteria, where an amine may be included to attenuate the toxin.

Knowledge of the simple structure of a diaminoalkane as a potent inhibitor of toxin activity will enable those of skill in the art to identify receptors associated with pathogenicity as well as treat infectious diseases caused by pathogenic bacteria. Thus, such receptors are also within the scope of this invention.

The specific identification of other compounds within the scope of the invention is well within the ability of those in the art in light of the information conveyed by the present specification. In addition to describing the family of compounds, we have also provided the details of at least three assays to assess the protective ability of the antivirulence agents of the invention: the rabbit ileal loop assay, the Ussing chamber assay, and the transepithelial migration of polymorphonuclear leukocytes (PMN) assay. All three assays are accepted virulence assays and well within the routine skill of those in this art. A fourth accepted assay is the Séreny test, which tests for virulence by presence of the ability to induce keratoconjunctivitis in the guinea pig eye (Sansonetti, P. J., et al. (1983) *Infect. Immun.* 39, 1392–1402).

In addition, as would be understood by those in the art, the protection against enterotoxins could be used to prevent and/or to treat hosts suffering from enteropathogenic and gastrointestinal disorders such as diarrhea, dysentery and hemorrhagic colitis. As would also be understood in the art, prevention of such disorders is achieved when the host does not exhibit any of the physical symptoms of these gastrointestinal disorders. Treatment, or attenuation of symptoms, is achieved by the complete or partial amelioration of the physical symptoms as described previously.

In addition, the determination of the appropriate dosage or effective amount and the frequency of administration for use with the compounds of the invention is well within the skill of those in this art. These will depend on the potency and duration of action of the organisms or compounds used; but also on the nature and severity of the disease to be treated and on the sex, age, weight and individual responsiveness of the host to be treated. The hosts of the invention may be any animal but are preferably mammals with humans as particularly preferred hosts. Other examples are animals of economic importance such as cows, pigs, and chickens as well as animals commonly kept as household pets.

The invention includes the compounds described above together with any pharmaceutically acceptable carrier. Carriers can be sterile liquids, such as water, oils, including petroleum oil, animal oil, vegetable oil, peanut oil, soybean oil, mineral oil, sesame oil, and the like. With intravenous administration, water is a preferred carrier. Saline solutions, aqueous dextrose, and glycerol solutions can also be employed as liquid carriers, particularly for injectable solutions. Suitable pharmaceutical carriers are described in Remington's Pharmaceutical Sciences, 18th Edition (A. Gennaro, ed., Mack Pub., Easton, Pa., 1990), incorporated by reference. The composition may also be formulated with stabilizers, adjuvants and other components.

Another aspect of the invention relates to use of the cadA gene, fragments thereof, and constructs based thereon (as well as other genes encoding amino acid decarboxylases) as a way of attenuating pathogenicity. For example, one of the persistent problems associated with the development of live, attenuated strains of Shigella as vaccines or vaccine vectors is the high degree of reactogenicity associated with the strains currently being studied (Kotloff, K. L., et al. (1996) *Infect. Immun.* 64, 4542–4548). It has been proposed that the ShET-1 and ShET-2 toxins of *S. flexneri* are responsible for the diarrhea that is seen in safety trials with volunteers. The transformation of pathogenic bacteria by introducing, for example, cadA or fragments thereof would inhibit the enterotoxicity of the toxins produced by the bacteria and thereby produce less toxic and, correspondingly, safer and more easily tolerated vaccines. One of skill in the art would understand the term vaccines to encompass vaccines derived from live attenuated bacteria, killed bacteria, bacterial components, conjugate vaccines, proteosome vaccines, and nucleoprotein (ribosomal) vaccines (WHO, Weekly Epidem. Record (1997)72:73–80 and references cited therein).

The introduction of such genes may also be applied to bacterial vectors such as *Salmonella typhimurium, Salmonella typhi, E. coli* and *Vibrio cholerae*. Although these pathogens do contain the gene for LDC and do synthesize the enzyme under laboratory conditions, it is possible that the bacteria repress the expression of LDC under in vivo host infection conditions. The introduction of such genes that encode LDC or other such enzymes in such a way as to promote constitutive expression would facilitate the development of safer and more easily tolerated vaccines.

Another advantage of such a process is the generation of a vaccine that protects the target host without diminishing or otherwise reducing the full antigenic complement of the bacteria (such as Shigella or any other enteroinvasive bacteria) administered. Unlike a vaccine strain in which the toxin genes have been deleted, such a construct will still produce toxins, thus exposing the host's body to the maximum number of potential antigenic sites. Another advantage over deleted vaccine strains is that such a constructed vaccine would be easily biochemically distinguishable from natural isolates due to pathogen exposure.

Additionally, utilizing LDC expression for attenuating toxicity has the advantage of simplifying strain construction, as a single gene cassette introduction is simpler than knockout mutagenesis of at least two toxin genes (as claimed in U.S. Pat. No. 5,589,380, Fasano et al.). In addition, as noted above, multigene deletions in the Shigella genome often continue to be reactogenic (Kotloff, K. L., et al. (1996)).

Finally, the introduction of cadA may also facilitate the development of DNA vaccines in which Shigella strains are used as vectors (Sizemore, D. R., et al. (1995). Fennelly, G. J. et al. (1999) *J. Immunol.* 162:1603–1610). Additional DNA or genes which may be added to form such vaccines are derived from, for example, HIV antigen, nucleoprotein or hemagglutinin of the influenza A virus or of the measles virus, *Mycobacterium tuberculosis* secreted proteins, or hantavirus glycoproteins and nucleocapsid proteins. One of skill in the art would recognize other appropriate genes or DNA.

Expression of LDC may also be able to inhibit the characteristic intense inflammatory response generated in the Shigella infected host, a response which is heralded by the migration of polymorphonuclear leukocytes (PMN) across the mucosal barrier to the site of the bacterial infection. Induction of PMN migration is a safe and acceptable ill vitro assay for such an inflammatory response in vivo. Cadaverine exhibits inhibition of PMN migration in a dose dependent fashion, and cadA insertion prohibits the PMN response to Shigella as set forth in Example 8.

Another embodiment of the invention relates to the correlation with pathogenicity of the deletion of a large section of the genome covering the region around cadA. As set forth in Example 1, we have determined that all four species of Shigella and EIEC have undergone this type of large deletion around cadA. When compared to the closest related nonpathogenic commensal *E. coli*, this deletion represents a "black hole" in the genome that serves to enhance pathogenicity of Shigella. Thus, in addition to the "pathogenicity islands" proposed as a major pathogen evolution mechanism (Hacker, J., et al. (1997) *Mol. Microbiol.* 23, 1089–1097), we believe that "black holes," the loss of commonly inherited genes that are incompatible with virulence ("antivirulence genes"), results in the creation of pathogenic bacteria.

This relates to yet another embodiment of the invention which has general relevance to many pathogens: the identification of genetic loci that are relevant to bacterial pathogenicity. Specifically, the method for identifying absent (deleted) genomic DNA in pathogenic strains which is present in non-pathogenic variants of the same or closely related species may be applied to other bacterial pathogens by comparing their genomes with the genomes of the closest related non-pathogen. These comparisons have the power to illustrate where in the genome pathogenicity lurks. Moreover, the identification of the missing genetic loci in the black hole will identify potential genes, gene products, and compounds enzymatically produced by the gene products which are incompatible with pathogenicity and thereby can provide new compounds for the treatment of disorders induced by the pathogen which are inhibitory to the bacterial pathogen (as we have successfully shown for LDC and cadaverine).

Some examples of useful genome comparisons, based on this principle, are listed as follows. One of skill in the art would be able to identify further pathogens and non-pathogens which are closely related. This pairing will facilitate the discovery of new inhibitors of pathogenicity, as well as new pharmaceutical candidates.

| Pathogen | Related non-pathogen |
|---|---|
| enteropathogenic *E. coli* | *Escherichia coli* normal |
| enterohemorrhagic *E. coli* | commensal isolates from human |
| enterotoxigenic *E. coli* | or animal intestinal tract |
| enteroaggregative *E. coli* | |
| uropathogenic *E. coli* | |
| meningitis-causing *E. coli* K-1 | |
| *Yersinia pestis* | environmental *Yersinia* isolates |
| *Yersinia pseudotuberculosis* | |
| *Yersinia enterocolitica* | |
| *Mycobacterium tuberculosis* | *Mycobacterium smegmatis* |
| *Mycobacterium bovis* | *Mycobacterium microti* |
| *Mycobacterium avium* | |
| *Neisseria gonorrhoeae* | *Neisseria cinerea* |
| *Neisseria meningitidis* | *Neisseria lactamica* |
| *Listeria monocytogenes* | *Listeria innocua* |
| *Vibrio cholerae* | aquatic vibrios |
| *Streptococcus pyogenes* | non-pathogenic streptococci |
| *Haemophilus influenzae* | Haemophilus from healthy individuals |

To promote a fuller understanding of this invention, we present the following examples. These examples do not, however, limit in any way the scope of the invention.

EXAMPLE 1

Bacteria and Genetic Manipulations

A. Bacterial Strains and Media

The bacterial strains used in our work are listed in Table 1 below.

TABLE 1

Bacterial strains

| Strain | Description | Source or reference |
|---|---|---|
| 2457T | *S. flexneri* 2a wild type | Formal, S. B., et al. (1958) J. Bacteriol. 75, 604–610. |
| BS103 | Plasmid-cured derivative of 2457T | Maurelli, A. T., et al. (1984) Infect. Immun. 43. 397–401. |
| BS226 | 2457T spa47::lacZ | Hromockyj, A. E. and A. T. Maurelli, (1989) Infect. Immun. 57:2963 |
| BS228 | 2457T ipaB::lacZ | Hromockyj, A. E and A. T. Maurelli(1989) |
| BS260 | 2457T mxiA::lacZ | Andrews, G. P., et al. (1991) Infect. Immun. 59:1997–2005 |
| BS529 | 2457T transformed with pCADA (cadA) | Maurelli, A. T. et al. (1998) PNAS USA 95:3943–3948 |
| BS573 | BS103 zii-215::Tn10dCamRCP2 zjh-225::Tn10dSpcRCP2 | Maurelli, A. T. et al.(1998) |
| MC4100 | *E. coli* K-12 prototype | Casadaban, M. J. (1976) J. Mol. Biol. 104, 541–555 |
| MG1655 | *E. coil* K-12 prototype | B. Bachmann* |
| CAG18427 | MG1655 zje-2241::Tn10 | Singer, M., et al. (1989) Microbiol. Rev. 53, 1–24 |
| χM2115 | MG1655 zii-215::Tn10dCamRCP2 | Bloch, C. A., et al. (1996) BBRC 223, 104–111 |
| χM2125 | MG1655 zjh-225::Tn10dSpcRCP2 | Bloch, C. A., et al. (1996) |
| χM2500 | MG1655 zii-215::Tn10dCamRCP2 zjh-225::Tn10dSpcRCP2 | Maurelli, A. T. et al. (1998) |

*E. coli* Genetic Stock Center

Strains were grown at 37° C. in Luria-Bertani medium (LB) with aeration, on LB agar, or on M9 minimal salts with glucose (Miller, J. H. (1972) *Experiments in Molecular Genetics* (Cold Spring Harbor Lab. Press, Plainview, N.Y.)). Media were supplemented with thiamine (50 µg/ml), spectinomycin (100 µg/ml), kanamycin (50 µg/ml), or chloramphenicol (15 µg/ml) as required. To optimize enterotoxin production, bacteria were grown in LB with ethylenediamine-N,N'-diacetic acid to chelate iron. Cultures of *E. coli* for measurement of LDC activity under inducing conditions were grown in medium buffered with 100 mM 4-morpholineethanesulfonic acid to pH 5.5 (Meng, S-Y. & Bennett, G. N. (1992) *J. Bacteriol.* 174, 2659–2669). Supernatants from overnight cultures of bacteria were harvested by centrifugation, filter-sterilized, and placed on ice until used.

B. Genetic Manipulations pCADA is a plasmid that contains the wild-type cadA gene from *E. coli* K-12 under the transcriptional control of the lac promoter (Meng, S-Y. & Bennett, G. N. (1992)). The cadA gene in pCADA is expressed constitutively in *Shigella flexneri* because of the absence of lac repressor in the organism and the plasmid vector. Generalized transduction with P1 was as previously described (Miller, J. H. (1972)). *E. coli* MG1655 mutants containing Tn10dSpcRCP2 or TN10dCamRCP2 insertions were generated by electroporation with plasmids pGI300 or pGI310 as described (Mahillon, J., Rode, C. K., Leonard, C. & Bloch, C. A. (1997) *Gene* 187, 273–279). MG1655 double insertion mutants and single and double insertion mutants of *S. flexneri* 2a strain BS103 were generated by transducing recipient strains with P1Δdam rev6 lysates of MG1655 insertion mutants (Bloch, C. A., et al. (1994) *J. Bacteriol.* 176, 7121–7125).

Genomic DNA was purified from 5.0 ml of overnight cultures of *E. coli*::Tn10dRCP2 and *S. flexneri*::Tn10dRCP2 mutants in a manner suitable for yielding macrorestriction fragments (0.05–1.0 Mb) as described (Rode, C. K., et al. (1995) *Gene* 166, 1–9). After digestion of agarose-embedded DNA with I-SceI (Boehringer Mannheim) for 1 hr or with I-CeuI (Panvera, Madison, Wis.) overnight, according to the manufacturers' directions, reaction buffer was decanted, and dots were melted (70° C.) and gently pipetted into sample wells in 1.3% agarose (Fastlane, FMC) gels for electrophoresis in a Bio-Rad DR-III pulse field gel apparatus. Pulse times were ramped from 10 to 13 s over 10 h and 60 to 65 s over 12 h at a field strength of 6 V/cm. After electrophoresis of samples, gels were analyzed as described (Heath, J. D., et al. (1992) *J. Bacteriol.* 174, 558–567).

FIG. 1 shows pulsed-field gel electrophoresis separation of genomic segments delimited by a pair of Tn10dRCP2 insertions. Lanes 1 and 8 show yeast-chromosome and λ-concatemer standards. Lanes 2, 3, 6, and 7 are I-CeuI digests of MG1655 (parent *E. coli* K-12), χM2500 (K-12 double-insertion mutant), BS573 (*S. flexneri* 2a double-insertion mutant), and BS103 (parent *S. flexneri* 2a), respectively. Lanes 4 and 5 show χM2500 and BS573 digested with I-SceI. The MG1655 native I-CeuI fragments of 130 and 670 kb were cleaved into pairs of sub-fragments of 30 and 100 kb and 235 and 435 kb, respectively, in the double insertion mutant χM2500, as predicted from the NotI and BlnI map coordinates of its insertions (Bloch, C. A., et al. (1996) *BBRC* 223, 104–111) and the native I-CeuI map (Liu, S.-L., et al. (1993) *Proc. Natl. Acad. Sci. USA* 90, 6874–6878). The I-CeuI pattern of genomic DNA from strain BS573 (containing the identical two insertions in the BS103 background) showed a new sub-fragment of 135 kb (consistent with cleavage and lack of change in migration of the largest native I-CeuI fragment) and a pair of sub-fragments of 40 and 100 kb from cleavage of one of two 140-kb native I-CeuI fragments, consistent with P1 transduction fidelity between strains and with genetic map conservation judged by rrl gene architecture (Liu, S.-L., et al. (1993)). Digestion of χM2500 and BS573 with I-SceI resulted in isolated bands allowing side-by-side comparison of a pair of I-SceI restriction fragments (398 $kb_{MG1655}$ and 205 $kb_{BS103}$) with corresponding end points from the MG1655 and BS103 backgrounds. White bars indicate the wild-type I-CeuI fragments missing because of Tn10dRCP2 insertion, and black bars indicate the corresponding I-CeuI sub-fragments generated (FIG. 1).

Genomic DNA for Southern blotting was prepared by standard methods (Ausubel, F. M., et al. (1997) *Current Protocols in Molecular Biology* (Wiley, N.Y.)). Southern hybridization of dot blots was done by spotting 10 µg of genomic DNA onto nylon or nitrocellulose filters (GENESCREEN™, Dupont/NEN, for example) and hybridizing with oligonucleotide probes end labeled with digoxigenin (DIG/Genius labeling kit, Boehringer Mannheim). Blots were processed with CSPD® (Tropix; disodium 3-(4-methoxyspiro (1,2-dioxetane-3,2'-(5'-chloro)tricyclo [3.3.1.13,7]decan)-4-yl)phenyl phosphate, available from Boehringer Mannheim), or other alkaline phosphatase substrate, for chemiluminescence according to the manufacturer's instructions.

Figure 2:
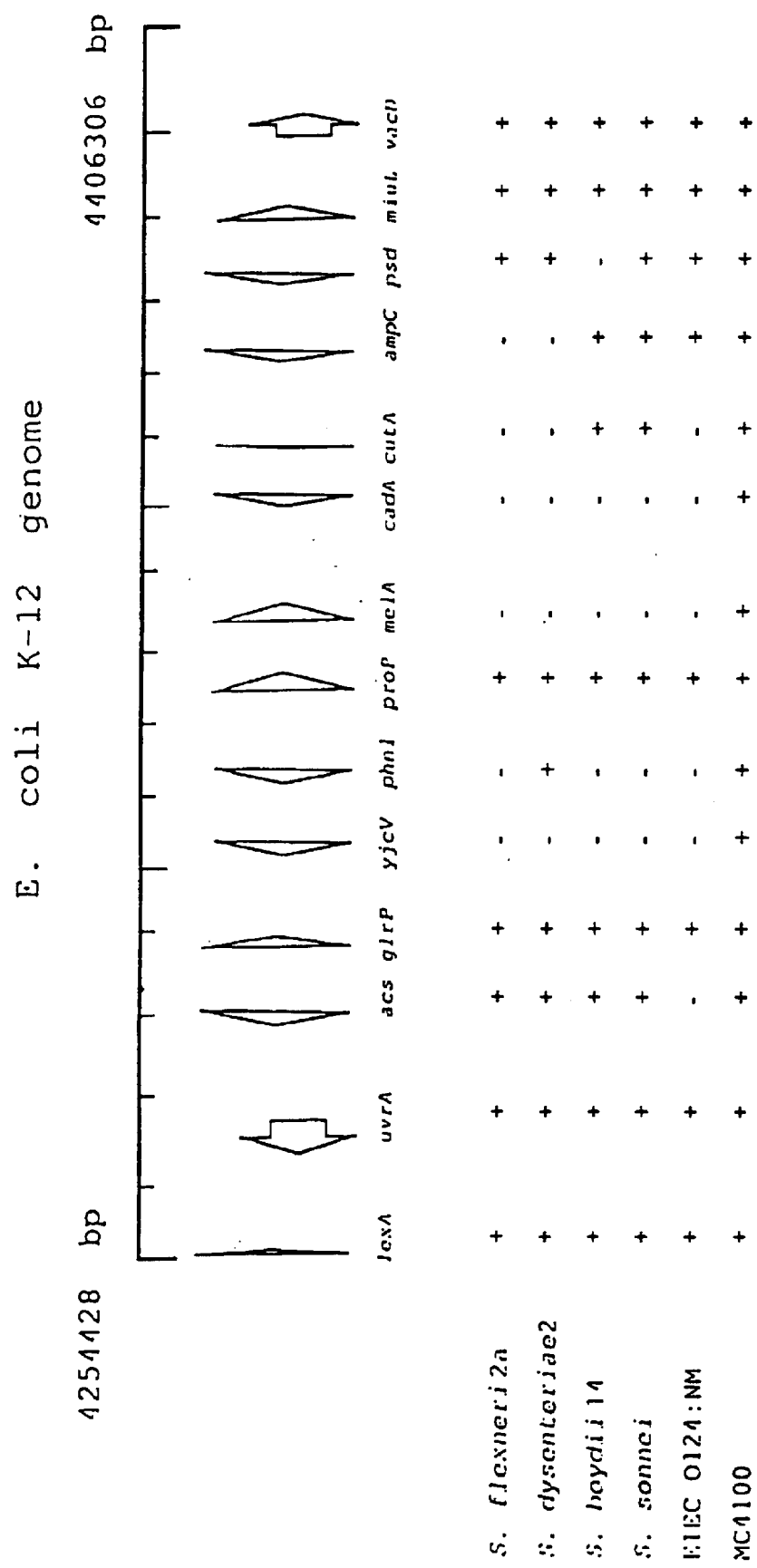
FIG. 2 is a schematic representation of bacterial pathogen genomes and their Southern blot hybridization, illustrating the "black holes" associated with pathogenicity.

FIG. 2 shows the schematic representation of data obtained from Southern blotting to show the "black holes" in the genomes of Shigella spp. and EIEC. The oligonucleotide probes used were from 14 different *E. coli* genes between base pair 4254428 and base pair 4406306, and were hybridized to the genomic DNA from these species. A negative sign indicates lack of hybridization, while a positive sign shows a positive hybridization response. All strains can be obtained from the ATCC, or as here, from Dr. Nancy Strockbine, Centers for Disease Control and Prevention. *S. flexneri* 2a (2457T) in this experiment was from our laboratory, but can also be obtained from the ATCC.

EXAMPLE 2

Virulence Assays

A. Cell, Plaque, and Ileal Loop Assays

The tissue culture cell invasion and plaque assays have been described (Hromockyj, A. E. & Maurelli, A. T. (1989) *Infect. Immun.* 57, 2963–2970). The rabbit ileal loop assay was performed essentially as described (Fasano, A., et al. (1990) *Infect. Immun.* 58, 3717–3723). Briefly, adult New Zealand white rabbits were starved for 24 h, but were allowed water ad libitum, and then were anesthetized with ketamine (50 mg/kg body weight) and acepromazine (1 mg/kg), followed by xylazine (7 mg/kg) i.m. Uninoculated LB and sterile culture supernatants (1 ml) were injected into the lumen of the intestine proximal to a tie placed near the mesoappendix. A second tie isolated the site of inoculation. Proceeding proximally along the ileum, five loops (7–8 cm long and separated by double ties) were isolated and inoculated. The sequence of inoculation of loops with the different preparations was randomized so that it varied from rabbit to rabbit. After 18 h, the animals were killed and fluid volume and the length of the loops were measured.

B Ussing Chamber Assays

Ussing chamber experiments were performed as described previously (Fasano, A., et al. (1991) *PNAS USA*

88, 5242–5246). In brief, adult New Zealand white rabbits were killed by cervical dislocation, and a 20-cm segment of distal ileum was excised quickly and cut open along the mesenteric border. The ileum was rinsed free of luminal contents, stripped of the muscular and serosal layers, and mounted in LUCITE® (clear plastic, Dupont) Ussing chambers (aperture 1.12 cm$^2$, World Precision Instruments, Sarasota, Fla.). The tissue was bathed in Ringer's solution at 37° C. and gassed with 95% $O_2$/5% $CO_2$. Once the tissue reached a steady-state condition, 300 µl of sterile culture supernatant was added to the mucosal side of the tissue. Sterile culture supernatant (300 µl) also was added to the serosal side to preserve the osmotic balance. Supernatants of S. flexneri strain 2457T also were tested in the presence of either 300 µl of supernatant from S. flexneri strain BS529 or increasing concentrations of cadaverine. In a subset of experiments (further described below), the intestinal epithelium was pretreated for 30 min with cadaverine (300 µM), washed twice with fresh Ringer's, and then exposed to 300 µl of 2457T (wild type S. flexneri 2a) supernatant.

Once the tissues were exposed to the above treatments, the potential difference (PD; the difference in voltage between the mucosal and serosal sides of the tissue) was measured under open-circuited conditions. The increase in voltage resulting from the passage of 100 µA current was used to calculated the short circuit current (Isc; the amount of current needed to nullify the PD) and the tissue resistance from Ohm's law (Isc=PD/tissue resistance) (Fasano, A., et al. (1991)).

C. Polymorphonuclear Leukocyte Migration Assays

As in the above virulence assays, wild-type S. flexneri 2a strain 2457T was compared to BS529 (LDC+) and to BS103 (avirulent). Monolayers of T84 cells, modeling human intestinal epithelium, were used to measure the ability of lysine decarboxylase expression and cadaverine to inhibit pro-inflammatory events. The migration of PMN across model intestinal epithelium was measured by counting cell equivalents on either side of the model membrane as a function of bacterial strain and the presence or absence of cadaverine.

EXAMPLE 3

Activity of Lysine Decarboxylase (LDC)

Of interest, one class of pathogenic E. coli, the enteroinvasive E. coli (EIEC), resembles a genetic hybrid between E. coli and Shigella. EIEC carry plasmids with extensive homology to the virulence plasmid of Shigella and cause a diarrheal disease that is clinically similar to dysentery cause by Shigella (Sansonetti, P. J., et al. (1985) in Microbiology— 1985, ed. Schlesinger, D. (Am. Soc. Microbiol., Washington, DC), pp. 74–77). One of the striking biochemical features shared by EIEC and Shigella is a lack of lysine decarboxylase (LDC) activity. Whereas almost 90% of E. coli strains are LDC$^+$ (Edwards, P. R. & Ewing W. H. (1972) Identification of Enterobacteriaceae (Burgess, Minneapolis), 3rd Ed.), all strains of EIEC and Shigella spp. are LDC$^-$ (Silva, R. M., et al. (1980) J. Clin. Microbiol. 11, 441–444). This observation suggested the possibility that absence of LDC activity may be important for Shigella and EIEC virulence. Assays for LDC activity were those of Falkow (Falkow, S. (1958) Am. J. Clin. Pathol. 29, 598–600) and Phan et al. (Phan, A. P. H., et al. (1982) Anal. Biochem. 120, 193–197). The former assay provided a qualitative measure of LDC activity based on a shift in pH from acid to alkaline due to the production of cadaverine from the decarboxylation of lysine. The bacteria are grown in lysine decarboxylase broth which contains the indicator bromocresol purple (Aldrich). As the bacteria grow in the broth, they ferment dextrose, resulting in an acid pH. Bacteria that produce lysine decarboxylase will decarboxylate lysine and produce cadaverine, which as a base, increases the pH of the medium. The test results are read after 24–96 hours as a purple or violet color (alkaline) for lysine decarboxylase producing bacteria and a yellow color (acid) for bacteria not producing the decarboxylase. Qualitative LDC results are indicated by a positive or negative sign in Table 2. The latter assay measured cadaverine produced from lysine based on the differential solubility of the reaction products of 2,4,6-trinitrobenzenesulfonic acid with cadaverine (>98% pure, Sigma) and lysine. Cadaverine reacts with TNBS to form N,N'-bistrinitrophenylcadaverine (TNP-cadaverine) which is soluble in toluene (but water insoluble). Lysine reacts with TNBS to form N,N'-bistrinitrophenyllysine which is not soluble in toluene (but is water soluble). TNP-cadaverine is extracted into the organic phase and the amount of TNP-cadaverine is measured spectrophotometrically at 340 nm. The concentration of cadaverine is then determined from a standard curve. Media blanks were used in both assays to control for trace amounts of amines and amino acids in the culture supernatant.

EXAMPLE 4

Correlation of cadA Expression and Shigella Virulence

Our initial failure to construct an LDC$^+$ derivative of S. flexneri by transducing cadA (E. coli K-12 map position 93.83 min (Tabor, H., et al. (1980) J. Bacteriol. 144, 952–956), the gene for LDC, into 2457T suggested that the S. flexneri chromosome may have a large deletion in the cadA region relative to the E. coli K-12 genome (the rare transductants recovered we surmised were the result of illegitimate recombination events). This was confirmed by PCR amplification with primers flanking the coding sequence of cadA (GenBank database accession no. M76411 and Meng, S-Y. & Bennett, G. N. (1992)) from genomic DNA of representative isolates of Shigella spp. (four strains) and EIEC (one strain). No PCR products were observed from the five toxin producing strains, whereas the positive control, E. coli K-12 strain MC4100, gave the expected 1.9-kb PCR product. Further evidence for the absence of the entire cadA gene was the failure to detect a hybridizing band in a southern blot of genomic digests from the same Shigella and EIEC strains by using a 2.6-kb fragment containing cadA from pCADA as a probe. The only exception was a strain of S. sonnei that yielded a positive hybridization signal when the cadA probe was used. Nevertheless, this strain was consistently negative in assays for LDC activity. These results and the inability to transduce markers from this region of E. coli K-12 into S. flexneri 2a (see above) suggested that Shigella spp. and EIEC have deleted a large region of the chromosome around the cadA locus.

An alternative cloning of a copy of cadA from E. coli K-12 into S. flexneri 2a strain 2457T via transformation did generate an LDC$^+$ derivative of S. flexneri. Resulting transformant BS529 expressed LDC activity, and when tested for expression of virulence phenotypes, it invaded HeLa cells and produced plaques as efficiently as the wild-type parent strain (data not shown). Thus, expression of cadA had no discernible effect on Shigella virulence in tissue culture invasion assays. This is in contrast to the remarkable effect of cadA on enterotoxin activity as measured in the Ussing chamber assay (see Table 2).

To obtain further evidence of the Shigella deletion detected above, *E. coli* insertion alleles carrying rare restriction sites were used to measure chromosomal distances between corresponding loci in *E. coli* K-12 and *S. flexneri* 2a. Two mini Tn10dRCP2 insertions flanking cadA in *E. coli*, carrying both the I-SceI and I-CeuI restriction sites and different antibiotic resistance genes (Bloch, C. A., et al. (1996)), were mobilized individually by P1 transduction from *E. coli* K-12 strains χM2115 and χM2125 into MG1655 (*E. coli* K-12) and BS103 (*S. flexneri* 2a). Any change in chromosomal distance between these two insertions, from the *E. coli* to *S. flexneri* backgrounds, then could be measured by a difference in the length of genomic DNA separating the new restriction sites introduced by them. Genomic DNAs from *E. coli* MG1655 and *S. flexneri* BS103 double-insertion mutants (χM2500 and BS573) were digested with I-SceI, whose recognition site of 18 bp is extremely rare and occurs only at the insertion sites (Monteilhet, C., et al. (1990) *Nucleic Acids Res.* 18, 1407–1413). As shown in FIG. 1 (lanes are described in detail in Example 1), these digests yielded I-SceI restriction fragments, the sizes of which indicated the distances between the two insertions in each background. These sizes of ≈398 and 205 kb, respectively (lanes 4 and 5), were consistent with an *S. flexneri* 2a deletion as large as 190 kb relative to *E. coli* K-12. Identical I-SceI fragments of 205 kb obtained from six separate BS103 transductants (data not shown) and similarities in the chromosomal organization of strains MG1655 and BS103 by I-CeuI restriction (FIG. 1) were consistent with P1 transduction fidelity and genetic map conservation, respectively, between strains.

To define roughly the limits of this large deletion in Shigella spp. and EIEC, we hybridized genomic DNA with oligonucleotide probes from 14 different genes 1–2 min clockwise and counter-clockwise of cadA. The results are shown in FIG. 2 and, as expected, indicate a large deletion (up to ≈90 kb) with variable end points in these representative strains. The hybridization pattern of the 14 probes in *S. flexneri* accounted only in part for the change detected by comparative macrorestriction mapping and suggested additional event(s) beyond the deletion of a contiguous segment in the region covered by the probes. Also, the retention in all isolates of hybridization to proP, which is surrounded on the K-12 map by deleted regions, suggested either a proP "island" flanked by deleted segments or the dislocation of proP by transposition or inversion to elsewhere in the Shigella spp. genome. In either case, retention of the proP gene would argue that the gene's function (low affinity transport for glycine betaine and proline) is beneficial to the bacteria. Experiments are underway to resolve the nature of the positive hybridization signal with the proP probe and to define precisely the end points of the deletion in *S. flexneri* 2a. Nevertheless, the hybridization results are consistent with the results in FIG. 1, and the large size of the deletion also explains the inability to transduce markers from this region of *E. coli* K-12 into *S. flexneri*.

EXAMPLE 5 cadA Expression Blocks Shigella Enterotoxicity in Ileal Loop Assay

Wild-type *S. flexneri* 2a produce enterotoxins whose activity can be measured by the ability to cause fluid secretion in ligated rabbit intestinal loops. Previous studies demonstrated that *E. coli*-Shigella hybrids from matings between a *S. flexneri* 2a donor and an *E. coli* K-12 recipient failed to induce fluid secretion in ligated rabbit ileal loops if the recombinants retained the LDC$^+$ phenotype of the *E. coli* recipient. By contrast, hybrids that inherited the *S. flexneri* region around 90 min and became LDC$^-$ induced fluid secretion as efficiently as the wild-type *S. flexneri* parent (Sansonetti, P. J., et al. (1983) *Infect. Immun.* 39, 1392–1402). Because of the large, undefined size of the DNA transferred in these experiments, it could not be determined whether the fluid secretion ability of the LDC-transconjugants was caused by the absence of cadA or inheritance of an unlinked toxin gene. Therefore we sought to determine whether BS529 expressing cadA could still induce fluid secretion by injecting supernatants of this strain into ligated rabbit ileal loops. Whereas the wild-type *S. flexneri* 2a parent 2457T caused an average of 0.6 ml fluid accumulation/cm, the LDC$^+$ strain BS529 induced no fluid accumulation in the ligated loop. These results indicated that expression of cadA alone was sufficient to block the ability of Shigella to induce fluid secretion in this assay.

EXAMPLE 6

Cell Free Supernatant Inhibits Enterotoxin in Ussing Chamber Assay

At least two iron-regulated enterotoxins produced by *S. flexneri* 2a are thought to be responsible for fluid accumulation in the ligated ileal loop assay. ShET1 is encoded chromosomally and present in all strains of *S. flexneri* and is only rarely encountered in other serotypes, and ShET2 (present in >80% of Shigella tested, see Nataro, J. P., et al. (1995) *Infect. Immun.* 63, 4721–4728) is encoded on the large virulence plasmid found in all strains of Shigella and EIEC (Fasano, A., et al. (1995) *J. Clin. Invest.* 95, 2852–2861; Noreiga, F. R., et al. (1995) *J. Infect. Dis.* 172, 1408–1410; Nataro, J. P., et al. (1995) *Infect. Immun.* 63, 4721–4728). Both toxins irreversibly alter electrolyte and water transport in rabbit intestine in vitro and in vivo (Fasano, A., et al. (1995), Nataro, J. P., et al. (1995), Fasano, A., et al. (1997) *Gut* 40, 505–511). Because the activity of these and other enterotoxins can be measured more precisely in Ussing chambers (Fasano, A., et al. (1997)), supernatants of BS529 were tested in this assay. Table 2 shows that the presence of the cadA gene in BS529 significantly inhibited enterotoxin activity relative to the parent strain. The ΔIsc values were even lower than the plasmid-cured strain (BS103) and suggested that the presence of the cad gene reduced both plasmid- and chromosome-encoded enterotoxin activities. Supernatants of BS529, when mixed with supernatants of wild-type *S. flexneri* 2457T, also were able to reduce dramatically the ΔIsc in a time-dependent fashion. This latter result suggested that the effect of cadA$^+$ was not at the level of toxin gene expression in BS529 but rather that it acted in trans on toxin that was present in the cell free supernatants.

TABLE 2

Enterotoxin activity of bacterial strains as measured in Ussing chamber assay*

| Strain | Enterotoxin produced | LDC activity | ΔIsc | P vs. 2457T† |
|---|---|---|---|---|
| 2457T (ΔcadA) | ShET1; ShET2 | – | 103.0 ± 19.0 | |
| BS103 (ΔcadA) | ShET1 | – | 78.1 ± 3.03 | not significant |
| BS529 (pCADA$^+$) | ShET1; ShET2 | + | 33.8 ± 13.1 | 0.04 |

TABLE 2-continued

Enterotoxin activity of bacterial
strains as measured in Ussing chamber assay*

| Strain | Entero-toxin produced | LDC activity | ΔIsc | P vs. 2457T† |
|---|---|---|---|---|
| 2457T + BS529‡ | ShET1; ShET2 | + | 56.0 ± 12.3 | 0.02 |
| 2457T + BS529§ | ShET1; ShET2 | + | 19.5 ± 4.3 | 0.0013 |

*Variations in transepithelial electrical PD, Isc, and total tissue resistance were recorded 120 min after addition or supernatants to chamber. PD measures the difference in electrical charges between the mucosal and serosal sides of the tissue and is generated by differences in concentrations of ions. Isc is the amount of current necessary tonullify the PD. Increase of both PD and Isc induced by enterotoxins reflects Cl secretion and is indicative of a diarrheagenic effect.
†Unpaired Student's t test.
‡ΔIsc measured 60 min after addition of supernatants to chamber.
§ΔIsc measured 120 min after addition of supernatants to chamber.

EXAMPLE 7

Cadaverine is the Secreted Enterotoxin Inhibitor

The Ussing chamber results indicated that the inhibiting factor resulting from expression of cadA in *S. flexneri* strain BS529 was associated with the culture supernatants. We hypothesized that this factor could either be LDC or a product of the reaction it catalyzes. LDC is a cytoplasmic protein and its export would be surprising. In contrast, cadaverine, a product of the decarboxylation of lysine by LDC, is secreted from LDC$^+$ cells (Meng, S-Y. & Bennett, G. N. (1992)). We quantified cadaverine present in supernatants of BS529 grown in LB by spectrophotometric assay (Phan, A. P. H., et al. (1982)). Whereas cultures of wild-type *S. flexneri* 2a strain 2475T contained no measurable cadaverine, BS529 supernatants contained 225–300 μM cadaverine. These levels are comparable to the amount of cadaverine produced by *E. coli* K-12 MC4100 under inducing conditions (data not shown and Meng, S-Y. & Bennett, G. N. (1992)). To determine whether pure cadaverine could mimic the supernatant-associated Shigella enterotoxins inhibitory effects in Ussing chamber assays, supernatants of 2457T were mixed with cadaverine, and toxin activity was measured. Table 3 shows that inhibition of enterotoxin activity of 2457T supernatants increased with increasing concentrations of cadaverine. When 300 μM cadaverine alone was added to the Ussing chamber, no difference in ΔIsc was observed, as compared with uninoculated LB. Thus, despite the charged nature of cadaverine, it has no electrical signaling effect in the Ussing chamber when used at a concentration that showed complete inhibition of the ΔIsc induced by 2457T supernatants.

TABLE 3

Effect of increasing concentrations of cadaverine on
*S. flexneri* 2a enterotoxin activity in Ussing chamber assay

| Concentration*, μM | ΔIsc | P vs. 2457T alone† |
|---|---|---|
| No cadaverine | 68.6 ± 6.5 | |
| 50 | 68.7 ± 21.5 | not significant |
| 100 | 52.1 ± 12.6 | not significant |
| 200 | 42.9 ± 5.5 | 0.039 |
| 300 | 2.7 ± 8.9 | 0.009 |
| 500 | −18.7 ± 14.1 | 0.007 |
| Uninoculated LB | −3.0 ± 14.9 | 0.005 |
| 300 cadaverine alone‡ | 7.9 ± 4.3 | 0.001 |

*2457T supernatant (300 μl) was added to both sides of the rabbit mucosa either alone or with cadaverine at the concentration indicated.
†Unpaired Student's t test.
‡No bacterial supernatant added.

To determine whether cadaverine directly inhibited the toxin(s) or acted to protect the host cells, tissues in the Ussing chamber were pretreated with 300 μM cadaverine for 30 min before being washed twice with Ringer's solution and then subjected to enterotoxin-containing supernatants from *S. flexneri* 2457T. Pretreatment with cadaverine reduced the ΔIsc to 40% of the value observed in tissues that had not been pretreated (61.5±19.8 vs. 153.6±25.5). This result suggested that cadaverine acted to protect the host cells before exposure to the toxins.

Our results suggest two possible models for the action of cadaverine: first, cadaverine inactivates the toxins synthesized by Shigella, or, second, cadaverine acts directly on the target cell to protect it. The first model would require that cadaverine be able to inhibit both ShET1 and ShET2 (and other undefined enterotoxins) produced by *S. flexneri*. Although the molecular mechanism of action of these two toxins has yet to be determined, we believe they act via different pathways. By contrast, the second model is supported by our results, which show that pretreatment of rabbit mucosa in the Ussing chamber with cadaverine protected the mucosa from the effect(s) of enterotoxins added after the cadaverine was washed from the tissue. Polyamines such as cadaverine are absorbed from the lumen by rabbit small intestine cells (Brachet, P., et al. (1995) *Am J. Physiol.* 269, 754–762), and it has been proposed that intracellular polyamines might act as second messengers in the eukaryotic cell by modulation of extracellular signals transduced through G protein-coupled receptors (Bueb, J. L., et al. (1992) *Biochem. J.* 282, 545–550). In this light, cadaverine could protect the cell by closing ion channels induced by bacterial toxins, altering intracellular signaling, or displacing toxin from cellular receptors. Analysis of these possibilities is one aspect of the present invention.

TABLE 4

Lysine Decarboxylase (LDC) Activity of Bacterial
Pathogens and the Effect of Cadaverine[1] on Toxins They Produce

| Bacteria | LDC Activity | Toxin | Virulence Assay | Effect of Cadaverine |
|---|---|---|---|---|
| *Shigella flexneri* 2a | negative | ShET-1 and ShET-2 | Fluid accumulation in ileal loops Enterotoxicity in Ussing chambers | both completely blocked |

TABLE 4-continued

Lysine Decarboxylase (LDC) Activity of Bacterial
Pathogens and the Effect of Cadaverine[1] on Toxins They Produce

| Bacteria | LDC Activity | Toxin | Virulence Assay | Effect of Cadaverine |
|---|---|---|---|---|
| *Shigella dysenteriae* 1 | negative | Shiga toxin | Enterotoxicity in Ussing chambers<br>Cytotoxicity in Vero cells | blocked;<br>none |
| *Yersinia enterocolitica* | negative | stable toxin (YST-I) | Enterotoxicity in Ussing chambers | completely blocked |
| *Bacterioides fragilis* | negative | BFT | Enterotoxicity in Ussing chambers | completely blocked |
| *Campylobacter jejuni* | negative | cytolethal distending toxin | Enterotoxicity in Ussing chambers | completely blocked |
| *Vibrio cholerae* O1 | positive | cholera toxin | Enterotoxicity in Ussing chambers | none |
| enterotoxigenic *Escherichia coli* | positive | heat stable toxin (STa) | Enterotoxicity in Ussing chambers | none |
| avian pathogenic *Escherichia coli* | positive | Tsh-associated toxin | | ND |
| enteroaggregative *Escherichia coli* | positive | EAST-1 | | ND |
| *Escherichia coli* 9142 | positive | cytolethal distending toxin | | ND |
| *Pseudomonas aeruginosa* | negative | exotoxin A | | ND |

[1]Cadaverine was used at 400 $\mu$M unless otherwise indicated.
N.D.: not determined.

TABLE 5

Lysine Decarboxylase (LDC) Activity and the Effect of Cadaverine
On Enterotoxic Activity in Ussing Chamber Assay

| Bacteria | LDC activity | Toxin | ΔIsc Toxin alone | ΔIsc + cadaverine[1] | P vs. control[2] |
|---|---|---|---|---|---|
| *Shigella flexneri* | negative | ShET-1 and ShET-2 | 68.6 | 2.7 | <0.001 |
| *Shigella dysenteriae* 1 | negative | Shiga toxin | 33.7 | −13.6 | <0.01 |
| *Yersinia enterocolitica* | negative | stable toxin (YST-1) | 65.1 | −11.0 | <0.005 |
| | | stable toxin (YST-11) | 46.8 | 32.4 | NS |
| *Bacteriodes fragilis* | negative | BET | 57.6 | 21.5 | <0.005 |
| *Campylobacter jeluni* | negative | Cytolethal distending toxin | 56.4 | −18.7 | <0.005 |
| *Vibria cholerae* O1 | positive | cholera toxin (CT) | 62.3 | 70.9 | NS |
| enterotoxigenic *Escherichia coli* | positive | heat stable toxin (STa) | 60.8 | 75.9 | NS |
| avian pathogenic *Escherichia coli* | positive | Tsh-associated toxin | 146.1 | 23.3 | ND |
| enteroaggregative *Escherichia coli* | positive | EAST-1 | ND | ND | ND |
| *Escherichia coli* 9142 | positive | Cytolethal distending toxic | ND | ND | ND |
| *Pseudomonas aeruginosa* | negative | Exotoxin A | ND | ND | ND |

[1]Toxins were added to the mucosal side of the tissue. Cadaverine (400 $\mu$M) was added to both mucosal and serosal sides of the tissue.
[2]Unpaired Student's t test. NS = not significant; ND = not determined

EXAMPLE 8

Cadaverine Blocks *S. flexneri* Induced PMN Transepithelial Migration

The PMN transepithelial migration assays were performed essentially as described previously, see, for example Hensen and Oades, (1975) *J. Clin. Invest.* 56 1053–1061; McCormack, S. A. et al. (1993) *Am. J. Physiol.* 264 G367–G374; Nash et al. (1987) *J. Clin. Invest.* 80:1104–113; Parkos et al. (1992) *J. Cell Biol.* 117, 757–764; Parkos et al. (1991) *J. Clin. Invest.* 88, 1605–1612. Briefly, human PMN were purified from whole blood (anticoagulated with citrate 13.2 g/dextrose 11.2 g in 500 ml water, pH 6.5) collected by venipuncture from normal human volunteers. The buffy coat was obtained via a 400× g at room temperature. Plasma and mononuclear cells were removed by aspiration, and the majority of erythrocytes were removed by a 2% gelatin sedimentation technique as described in Hensen and Oades (1975), and Parkos et al. (1991). Residual erythrocytes were then removed by gentle lysis in cold $NH_4Cl$ lysis buffer. This technique allowed for rapid isolation (90 min) of functionally active PMN that were 95% pure with 98% viability as determined by trypan blue exclusion. After isolation, PMN were suspended in modified HBSS (without $Ca^{2+}$ and $Mg^{2+}$ but with 10 mM HEPES, pH 7.4; Sigma) at 4° C. at a concentration of $5 \times 10^7$/ml and were used for experiments within an hour after isolation.

Prior to the addition of PMN in this assay system, confluent, inverted T84 polarized monolayers ($3.5 \times 10^5$ cell/well) (Madara et al., (1992) *J. Tissue Cult. Meth.* 14, 209–213; Parkos et al., (1991)) were rinsed extensively in HBSS(+) to remove residual serum components. Cultures of *S. flexneri* strains were prepared by washing the bacteria twice in HBSS(+) and resuspending in 300 µl buffer/10 ml culture (final concentration ~$1.5 \times 10^9$ bacteria per ml). For basolateral surface exposure, 25 µl of the bacterial suspension ($3.5 \times 10^7$ bacteria) was directly added to the upper compartment of T84 cell inverted monolayers (see below) at a multiplicity of infection at 100 bacteria/epithelial cell, subsequent to the removal of the basolateral buffer. In studies requiring apical surface exposure, inverted monolayers were removed from each well and placed in a moist chamber such that the epithelial apical membrane (lower compartment) was oriented upward. Again, 25 µl of the bacterial suspension was gently distributed onto the apical surface. For simplicity, the reservoir will be referred to by the epithelial membrane domain with which it interfaces (i.e., apical or basolateral). *S. flexneri* strains were incubated at the basolateral epithelial interface for 90 minutes at 37° C. Non-adherent bacteria were next removed by washing three times in HBSS(+) buffer and under those conditions it was determined that there were 80 cell associated bacteria/epithelial cell. The monolayers were then transferred into fresh 24-well tissue culture trays containing 1.0 ml of HBSS buffer in the bottom (apical) compartment and 100 µl in the top (basolateral) compartment. To the basolateral bath, 40 µl ($1 \times 10^6$) of isolated PMNs was added to each monolayer and incubated for 150 minutes at 37° C. Positive control transmigration assays were performed by the addition of chemoattractant (10 nM N-formyl-Met-Leu-Phe, fMLP; Sigma Chemical Co.) to the opposing apical reservoir. All experiments were performed in a 37° C. room to ensure that the epithelial monolayers, solutions, and plasticware, were maintained at a uniform temperature.

Transmigration was quantified by assaying for the PMN azurophilic granule marker myleoperoxidase, as described previously (Madara et al. (1992); McCormick et al. (1993); Parkos et al. (1992); Parkos et al. (1991)). After each transmigration assay, PMN cell equivalents (CE), were assessed as the number of PMN that had completely traversed the monolayer (i.e. into the apical reservoir). Since variation exists in both TER between groups of monolayers (baseline resistance range 650–1,500 ohm·cm$^2$) and in PMN obtained from different donors, individual experiments were performed using large numbers of monolayers and PMN from single blood donors on individual days. PMN isolation was restricted to 10 different donors (repetitive donations) over the course of these studies.

Cadaverine was reconstituted in water at a stock concentration of 20 mM. Subsequent dilutions were prepared in HBSS(+) to achieve concentrations of 100, 300, and 500 µM. To analyze the influence of cadaverine on the ability of *S. flexneri* to invade into the basolateral membrane of polarized T84 cell monolayers, bacteria were resuspended at a concentration of $5 \times 10^8$ ml in 1 ml of HBSS(+) containing either 100, 300, or 500 µM cadaverine. Bacteria in the continued presence of cadaverine was then added to the basolateral surface of inverted monolayers and assessed for their ability to adhere to and enter into the basolateral domain of T84 epithelial cell monolayers, as measured by standard procedures described above.

To analyze the influence of cadaverine on the ability of *S. flexneri* to induce PMN transepithelial migration, four supplementary experiments were performed. First, to assess the initial influence of cadaverine on the ability of *S. flexneri* to induce PMN transepithelial migration, the bacteria were reconstituted in either 100, 300, or 500 µM cadaverine and subsequently added to the basolateral surface T84 epithelial cell monolayers for 90 minutes. The ability of PMN to transmigrate across epithelial cell monolayers under these conditions were evaluated by standard procedures as described above. Second, to assess whether cadaverine acts directly on epithelial cells, the target cell, either the apical or basolateral membrane domain of T84 epithelial cell monolayers was pre-treated with 300 µM cadaverine for 30 minutes at 37° C. and washed prior to the addition of *S. flexneri*. Subsequently, PMN transepithelial migration was assessed according to established protocols as described above. Third, the ability of *S. flexneri* to induce PMN transepithelial migration was evaluated under conditions where 300 µM cadaverine was simultaneously added to the apical or basolateral epithelial cell surface at the same time that *S. flexneri* was added to the basolateral epithelial cell surface. Following a 90 minute incubation at 37° C., PMN transepithelial migration was assessed as described above. Finally, the direct influence of 300 µM cadaverine on peripheral blood PMN was examined. In these experiments, PMN were pre-treated with 300 µM cadaverine for 30 minutes at 37° C. prior to addition to the basolateral epithelial membrane domain, and PMN transmigration events were evaluated as described above. A positive control for PMN transmigration was established using imposed gradients of the potent chemotactic peptide fMLP (10 nM) for each treatment condition performed. A negative control consisted of monolayers incubated in the absence of chemoattractant and bacterial stimulus.

T84 intestinal epithelial cells (passages 46–66) were grown in a 1:1 mixture of Dulbecco-Vogt modified Eagles medium and Ham's F-12 medium supplemented with 15 mM HEPES (pH 7.5), 14 mM NaHCO$_3$, 40 mg/ml penicillin, 8 mg/ml ampicillin, 90 mg/ml streptomycin, and 5% newborn calf serum. Monolayers were grown on 0.33 cm$^2$ suspended collagen-coated permeable polycarbonate filters (Costar Corp., Cambridge, Mass.) and utilized 7–14 days after plating, as described previously in Madara and Darmsathapthorn (1985) *J. Cell Biol.* 101, 2124–2133; Madara et al. (1992); and Parkos et al. (1992). Inverted monolayers were then used to study invasion capacity of bacteria and transmigration of neutrophils in the physiological basolateral-to-apical direction. A steady state transepithelial cell resistance (TER), approximately 1,500 ohm cm$^2$, is reached in 5 days with variability largely related to cell passage number. Monolayers received one weekly feeding following initial plating.

Figure 3:
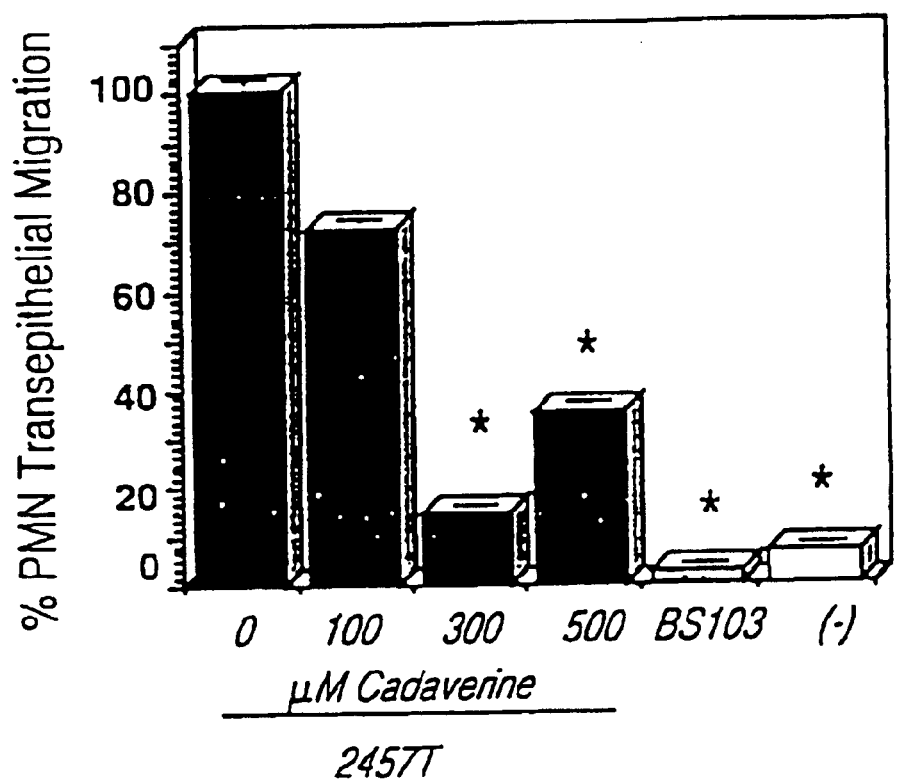
FIG. 3 shows a cadaverine dose response in the polymorphonuclear leukocyte migration assay (PMN) as described in Examples 2 and 8.

A. Dose Dependency of Cadaverine Attenuation of *S. flexneri*-Induced PMN Migration The role of cadaverine in blocking this pro-inflammatory response was examined to determine whether incubation of wild type *S. flexneri* 2a with cadaverine influenced the ability of the bacteria to induce PMN transepithelial migration. According to the procedure described previously, the basolateral surface of T84 epithelial cell monolayers were exposed in *S. flexneri* 2457T or BS103 together with cadaverine (100, 300, and 500 µM) and assessed for the ability to induce PMN transepithelial migration. The results of this assay are shown in FIG. 3, where the negative control (−) represents PMN transmigration to HBSS (+) buffer in the absence of bacteria or chemotactic stimulus. Data are expressed as mean±SEM for four monolayers in a single experiment and are representative of three separate experiments, all showing the same result. The asterisk indicates statistical significance vs. *S. flexneri* (2457T), where p<0.05. As shown in FIG. 3, we found that the addition of 2457T to the basolateral domain of T84 cell monolayers together with varying concentrations of cadaverine resulted in a dose dependent decrease in the ability of *S. flexneri* to promote PMN transepithelial migration. The cadaverine dependent abolishment of the transepithelial signaling of PMN induced by virulent *S. flexneri* confirmed the pharmaceutical potential of this type of compound, particularly in the treatment of shigellosis.

In order to confirm that this result was not caused by an effect of cadaverine on the bacteria, adherence and internalization assays were performed. As shown in Table 6, the presence of cadaverine at any of the concentrations tested (100–500 μM) showed no adverse effects on the capacity of 2457T to either adhere to or be internalized by T84 intestinal epithelial cells. Thus, the failure of *S. flexneri* 2a to induce PMN transepithelial migration in the presence of cadaverine is not due to inhibition of the organism's ability to invade intestinal epithelial cells in the presence of cadaverine.

TABLE 6

Effect of cadaverine treatment on the invasion capacity of Shigella.

| | % Association | | % Internalization | |
|---|---|---|---|---|
| | 2457T | BS103 | 2457T | BS103 |
| 0 | 3.08 ± 0.70 | 2.02 ± 1.00 | 0.70 ± 0.11 | 0.08 ± 0.02 |
| 100 μM | 4.49 ± 0.19 | 4.37 ± 1.64 | 0.52 ± 0.01 | 0.08 ± 0.02 |
| 300 μM | 6.01 ± 0.72 | 3.14 ± 0.75 | 0.40 ± 0.11 | 0.03 ± 0.01 |
| 500 μM | 4.00 ± 0.70 | 2.11 ± 0.90 | 0.50 ± 0.11 | 0.01 ± 0.01 |

Results are expressed as mean (%) ± SEM

B. LDC+ Bacteria Fail to Induce PMN Migration.

We sought to determine whether the expression of cadA by *S. flexneri* influenced the ability to induce pro-inflammatory events which govern PMN trafficking across intestinal epithelial monolayers. As in the previous assays, wild type *S. flexneri* 2a strain 2457T was compared to BS529 (LDC+), and BS103 (avirulent). Here we measured the ability to direct PMN transepithelial migration across model intestinal epithelia. When added to the basolateral surface of polarized T84 cell monolayers, only 2457T specifically induced signals necessary for PMN transepithelial migration $(1.05(\pm0.03) \times 10^4$ cell equivalents, CE per ml). The LDC+ transformant, BS529, failed to elicit PMN transmigration $(0.011 (\pm0.001) \times 10^4$ CE per ml). These values were similar to those of the negative controls (avirulent, plasmid-cured strain, BS 103 and buffer control) which also failed to induce PMN migration $(0.011 (\pm0.001) \times 10^4$ CE per ml). In these experiments the number of PMN induced to migrate by *S. flexneri*—epithelial interactions ranged from $1 \times 10^4$–$6 \times 10^4$, with variability largely due to blood donor variation and T84 cell passage number. The failure of BS529 to induce PMN transepithelial migration was not due to an inability of this strain to invade intestinal epithelial cells. We previously demonstrated the ability of BS529 to exhibit wild-type levels of epithelial cell invasion (Maurelli et al., 1998 and Examples). Therefore, these data indicate that expression of cadA, and hence LDC activity, by *S. flexneri* was sufficient to perturb the signaling cascades which govern Shigella-induced PMN transepithelial migration.

C. Cadaverine Pre-Treatment Attenuates *S. flexneri* Induced PMN Migration.

Figure 4:
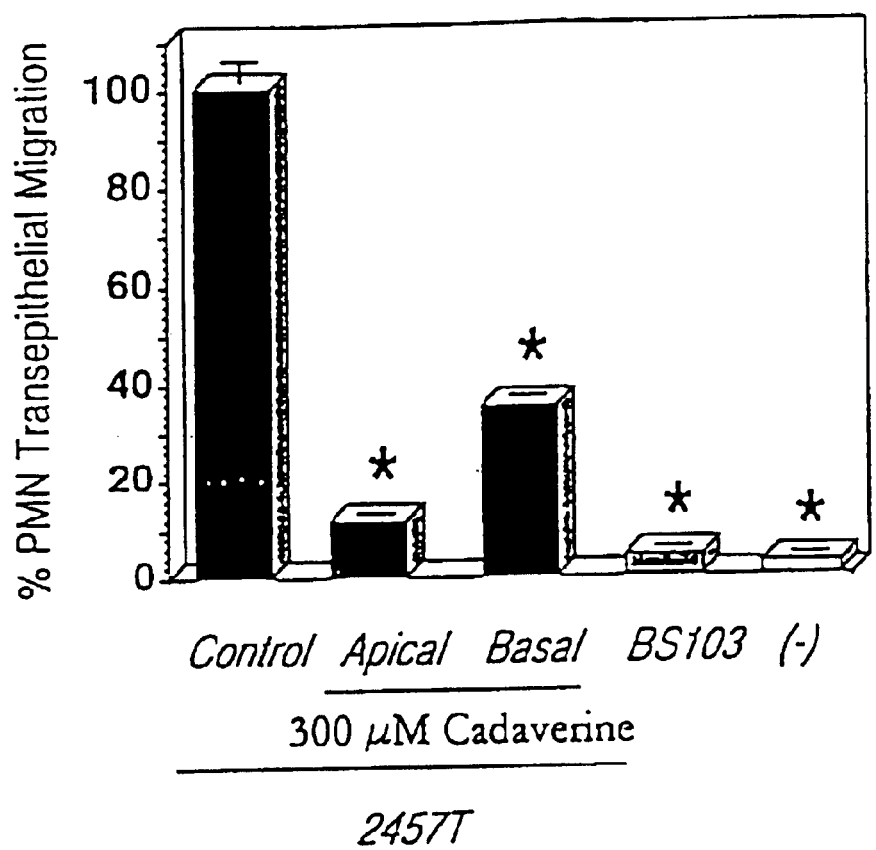
FIG. 4 shows the effect of cadaverine pretreatment of T84 monolayers in the PMN assay.

As shown in FIG. 4, pretreatment of the apical surface of T84 cells with 300 μM cadaverine at 37° C. for 30 minutes before washing and infection with 2457T at the basolateral epithelial membrane domain dramatically reduced the ability of this organism to induce PMN transepithelial migration. These results indicate that cadaverine acts on the target cell prior to bacterial exposure to block the signal pathway used by *S. flexneri* to induce PMN transepithelial migration. Pre-treatment of the basolateral surface of T84 cells with cadaverine also resulted in a substantial decrease in the ability of *S. flexneri* to induce PMN transepithelial migration, albeit to a lesser extent than that noted for apical pretreatment. Thus, while exposure of either epithelial cell membrane domain to cadaverine resulted in a marked attenuation of *S. flexneri*-induced PMN transepithelial migration, the strongest inhibition occurred through interactions at the apical epithelial membrane domain. T84 cells were pretreated with cadaverine (300 μM) at 37° C. for 30 min at either the apical or basolateral epithelial cell surface prior to infecting with 2457T at the basolateral epithelial cell domain, and subsequently assessed for the ability to induce PMN transepithelial migration. The negative control (−) is the same as Example 8A above. Data are expressed as mean±SEM for four monolayers in a single experiment and are representative of three separate experiments, all showing the same result. The asterisk indicates statistical significance vs. *S. flexneri* (2457T), where p<0.05. FIG. 4 shows that this pretreatment dramatically reduces the ability of the virulent bacteria to induce PMN transepithelial migration. The apical cell surface is preferred and generates a stronger inhibition compared to basal cell surface application.

D. Cadaverine Treatment on *S. flexneri* Infected T84 Monolayers Blocks PMN Migration.

Figure 5:
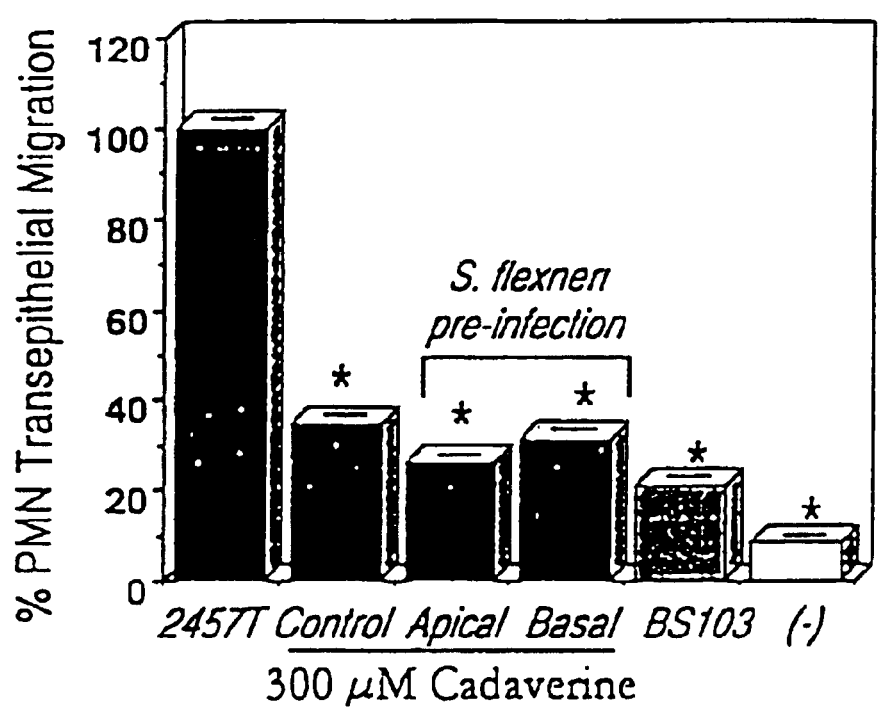
FIG. 5 illustrates the effect of cadaverine treatment on *S. flexneri* infected T84 monolayers in the PMN assay.

Having established that the apical surface of model intestinal epithelia can be targeted by cadaverine to down-regulate the signal cascades in Shigella-induced inflammatory responses, an important issue to address was whether cadaverine could down regulate *S. flexneri*-induced PMN transepithelial migration following established pathogen-epithelial cell interactions. This is a sequence of events which closely mimics the in vivo situation. Since bacterial-epithelial contact is required for eliciting pro-inflammatory responses which govern directed PMN transepithelial migration (McCormick et al (1998) *Infect. Immun.* 66, 4237–4243), we were able to permit *S. flexneri*-basolateral epithelial interactions to evolve (1 hr). The infected cell monolayers were then treated with cadaverine at the epithelial apical domain (30 min), washed, and then assessed for the level of transmigrated PMN across the epithelia. Notably, as shown in FIG. 5, treatment of *S. flexneri*-colonized T84 monolayers with cadaverine markedly down regulated (60%) the capacity of *S. flexneri* to orchestrate PMN transepithelial migration. The T84 cell basolateral membrane domain was infected with 2457T for 1 hour prior to the apical administration of cadaverine (300 μM), and subsequently assessed for the ability to induce PMN transepithelial migration. The negative control (−) is the same as Example 8A above. Data are expressed as mean±SEM for four monolayers in a single experiment and are representative of three separate experiments, all showing the same result. The asterisk indicates statistical significance vs. *S. flexneri* (2457T), where p<0.05. Therefore, as shown in FIG. 5, the efficacy of cadaverine treatment is not limited to conditions where model intestinal epithelia were treated with cadaverine prior to *S. flexneri* infection.

EXAMPLE 9

Identification of an "Anti-Virulence" Gene, a Gene Product, and an Enzymatically Produced Inhibitory Compound Via a Comparison Between Non-Pathogenic *Escherichia coli* K-12 and Pathogenic *Shigella flexneri*.

This example describes how the strategy described for cadA was used to identify another "anti-virulence" gene in Shigella and further compounds inhibitory to Shigella virulence.

As noted above, the genetic similarities between Shigella and *E. coli* are strong enough to justify placing them in the same genus. Shigella may even be considered metabolically inactive biogroups of *E. coli*. While the genetic similarities between Shigella spp. and *E. coli* are quite striking, there are several well known metabolic differences that distinguish the organisms. Among these are auxotrophic requirements of Shigella that are not found among isolates of *E. coli*. Most clinical isolates of Shigella fail to grow in minimal medium. Of these auxotrophic isolates, 98% grow in minimal medium supplemented with methionine, tryptophan, and nicotinic acid (Ahmed, Z. U., et al. (1988) *Infect. Immun.* 56:107–1009). It has been reported that the nicotinic acid auxotrophy of *S. flexneri* 2a strain191b is due to mutations at two unlinked loci, nadA (17 min.) and nadB (56 min.) (Gemski, P. Jr., et al. (1971) *Infect. Immun.* 3:500–503). On the other hand, nicotinic acid prototrophy can apparently be restored to *S. flexneri* 5 strain M90T by transformation with the cloned nadB gene from Salmonella (Mantis, N. J. and P. J. Sansonetti. (1996) *Mol. Gen. Genet.* 252:626–629). This data suggests a missing "anti-virulence" gene in the metabolic pathway, the product of which is a candidate for an inhibitor of Shigella virulence.

In *E. coli*, quinolinate is the precursor of nicotinamide adenine dinucleotide (NAD) and is synthesized from L-aspartate and dihydroxy-acetone-phosphate (DHAP). L-aspartate oxidase, encoded by the nadB gene, forms a multi-enzyme complex with quinolinate synthetase A, the gene product of nadA. This enzyme complex catalyzes the oxidation of L-aspartate to iminoaspartate which is then condensed with DHAP to form quinolinate. Quinolinate phosphoribosyltransferase, the product of the nadC gene, converts quinolinate to nicotinic acid mononucleotide which can then enter the pathway for NAD synthesis. In the absence of nadA or nadB, quinolinate is not made and this pathway to synthesis of nicotinic acid mononucleotide is blocked. Exogenous nicotinic acid, however, can be converted to nicotinic acid mononucleotide by the action of nicotinate phosphoribosyltransferase, the product of the pnc gene. In this way, the pathway for NAD synthesis is restored in a nicotinic acid auxotroph such as Shigella.

We tested our hypothesis that one or the other (or both) nad loci represent black holes in the genome of *S. flexneri* 2a 2457T. PCR primers flanking the nadB gene of *E. coli* are used to amplify the nadB locus from *S. flexneri* 2a. The PCR product is cloned and tested for a functional nadB gene product by transforming the cloned PCR product into a nadB mutant of *E. coli*. Growth of the transformants on minimal medium lacking nicotinic acid is proof of production of a functional L-aspartate oxidase encoded by the nadB gene amplified from *S. flexneri* 2a. Failure to complement the nicotinic acid auxotrophy of the *E. coli* nadB mutant is evidence that the nadB locus from *S. flexneri* is mutant. A similar approach is taken to clone and test the nadA locus of *S. flexneri* for functionality as evidenced by the cloned gene's ability to complement a nadA mutant of *E. coli*. This step identifies the anti-virulence gene(s).

The absence of either or both of these genes suggested that an intermediate in the pathway to synthesis of nicotinic acid mononucleotide could attenuate pathogenesis of Shigella, by the same logical method as we showed above for cadA. The ability of *S. flexneri* 2a strain 2457T to invade tissue culture cells was assayed in the presence and absence of nicotinic acid, nicotinic acid mononucleotide, or quinolinate. As shown in Table 7, quinolinate, the enzymatically produced compound of the product of the anti-virulence gene, at a concentration of 1 mM, did inhibit invasion of the monolayer cells by the bacteria. On the other hand, the compounds derived from genes which are compatible with virulence, nicotinic acid and nicotinic acid mononucleotide, had no effect. Nicotinic acid and nicotinic acid mononucleotide also had no effect on the motility of intracellular bacteria as evidenced by their ability to form fireworks (cytoplasmic projections) from the invaded cells. Pretreatment of the bacteria with quinolinate during exponential growth before addition of bacteria to the monolayers was not necessary to observe the inhibitory effect on invasion. The inhibitory action of quinolinate is observed even when the compound is present only during the invasion assay. This result suggests that quinolinate does not act primarily by inhibiting virulence gene expression, but rather exerts its inhibitory effect directly on the pathogenic bacteria to attenuate the bacteria's ability to invade the cells in the monolayer. The expression of lacZ operon (transcriptional) fusions to representative virulence genes supports this conclusion (Table 8) and shows that quinolinate treatment of *S. flexneri* 2a reduces virulence gene expression by only about 50%.

In summary, this example further demonstrates a novel, rational method for identifying new pharmaceuticals for the treatment of bacterial pathogenesis.

TABLE 7

Effects of NAD biosynthetic pathway components on the invasive phenotype of *S. flexneri* 2a strain 2457T.

| TREATMENT[1] | % INVASION[2] | % FIREWORKS |
|---|---|---|
| 2457T alone | 80 | 19 |
| 2457T + 1 mM nicotinic acid | 85 | 17 |
| 2457T + 1 mM nicotinic acid mononucleotide | 82 | 17 |
| 2457T + 1 mM quinolinate | 0.5 | 0 |

[1]The indicated supplements were present in the invasion assay only during the two hour invasion period.
[2]Values shown are averages from at least two independent experiments.

TABLE 8

Effect of quinolinate on virulence gene expression in *S. flexneri* 2a.

| Strains | Treatments | Miller Units of activity[1] |
|---|---|---|
| BS260 (mxiA::lacZ) | none | 501.3 ± 12.5 |
|  | 1 mM quinolinate | 196.5 ± 2.0 |
| BS226 (spa47::lacZ) | none | 587.3 ± 9.5 |
|  | 1 mM quinolinate | 312.3 ± 6.5 |
| BS228 (ipaB::lacZ) | none | 246.0 ± 19.3 |
|  | 1 mM quinolinate | 140.5 ± 2.9 |

[1]The results shown are averages of four independent experiments ± standard deviation. Measurement of β-galactosidase activity was performed as per Miller (1972).

EXAMPLE 10

Uses of Cadaverine and LDC+ Mutants for Vaccine Production

The potent inhibitory effect of cadaverine on Shigella enterotoxin activity poses a potential obstacle to full expression of the virulent phenotype in Shigella spp. and thus facilitates the development of a Shigella vaccine. We have shown that cadaverine does not block invasion, but does prevent the change in tissue resistance indicative of the undesirable diarrheic effect. Advantageously, transgenic LDC+ bacteria are immunogenically more effective as a vaccine, since only the action of the toxin is blocked. This is further developed by using these attenuated LDC+ bacteria as DNA vaccines, where the enteroinvasive action is exploited for gene delivery within the digestive system. Commonly known methods in the art are used to incorporate the cadA gene into the bacterial chromosomal DNA. The transformed bacterium produces LDC, which in turn secretes cadaverine and results in mediation of the toxin effects. The size and nature of the DNA encoding the cadA gene is varied according to the needs of the construct, including but not limited to, consideration of convenient restriction enzyme sites, any active fragments of the gene, which can be the entire gene or portions thereof (where "active" is meant to encompass the decrease in toxigenicity of enterotoxigenic toxins or production of functional lysine decarboxylase).

For example, the lysine decarboxylase gene is incorporated into a Shigella flexneri 2a vaccine strain. The following criteria are used to determine the genomic region to which the gene for lysine decarboxylase is targeted by recombination:

1. For optimal stability, cadA, the gene for lysine decarboxylase, is recombined into the bacterial chromosome.
2. The cadA gene is inserted into an intergenic region of the chromosome in order to avoid the problems of insertional gene inactivation and polarity.
3. The chromosome target area is linked to markers that provide positive selection for recombination of cadA.

The polymerase chain reaction (PCR) is used to amplify the cadA open reading frame (ORF) lacking the native promoter sequence from E. coli K-12 strain MC4100. A promoter to provide for constitutive expression of the cadA ORF is ligated next to the ORF. A region of the S. flexneri 2a chromosome that satisfies the above criteria is amplified by PCR from S. flexneri 2a. An example of such a region is the 4 kilobase hnr-galU-hns-tdk region. The cadA expression cassette is cloned into an intergenic region of this PCR amplification product from the S. flexneri 2a chromosome. The DNA fragment containing the cadA gene cloned into an intergenic region of hnr-galU-hns-tdk is called the cadA allelic exchange cassette. It is cloned into a plasmid such as pGP704, that has the properties of a suicide vector, i.e. conditional replication. This suicide vector carrying the cadA allelic exchange cassette is introduced into a strain of S. flexneri 2a that contains the galU::Tn10 allele. Selection for allelic exchange is made by selecting for growth on minimal galactose medium or on LB with fusaric acid. Bacterial colonies surviving this selection are tested for co-inheritance of the allelic exchange cassette containing the cadA gene (i.e. lysine decarboxylase activity) and loss of the galU::Tn10 allele (i.e. tetracycline sensitivity and ability to grow on galactose minimal medium). The genomic structure is verified by PCR and/or Southern blot. Loss of the suicide vector is confirmed by screening for the antibiotic resistance marker encoded on the vector backbone. In the example of pGP704, the marker on the suicide plasmid is ampicillin resistance. This strain contains the cadA gene expressed from a constitutive promoter stably incorporated into the chromosome of S. flexneri 2a. This strain serves as the donor to introduce the cadA gene into any vaccine strain of interest as described below.

A strain of Shigella spp. designed to be used as a vaccine strain or vector that has been attenuated for virulence by any of a variety of strategies known in the art (e.g. reduced invasion capacity, limited replication in vivo, reduced ability to spread within the epithelium, etc.) is transduced to tetracycline resistance using a P1L4 generalized transducing lysate prepared on a donor strain of S. flexneri 2a that contains the galU::Tn10 allele. The vaccine strain containing the galU::Tn10 allele is transduced with a P1L4 lysate prepared on the donor strain described above that carries the cadA gene expressed from a constitutive promoter stably incorporated into the chromosome. Selection is made for growth on minimal galactose medium or on LB with fusaric acid. Bacterial colonies surviving this selection are tested for co-inheritance of the allelic exchange cassette containing the cadA gene (i.e. lysine decarboxylase activity) and loss of the galU::Tn10 allele (i.e. tetracycline sensitivity and ability to grow on galactose minimal medium). The genomic structure is also verified by PCR and/or Southern blot.

A similar approach is used to clone and introduce the cadBA locus into a vaccine strain of Shigella. The cadB gene encodes a putative transporter of lysine into the bacterial cell and transport of cadaverine out of the cell. The inclusion of cadB in the vaccine strain (along with cadA) may improve attenuation by facilitating transport of cadaverine out of the bacteria in vivo.

The person skilled in the art would understand how to use and practice the invention based on the above disclosure. Other embodiments of the invention will be apparent to those skilled in the art from consideration of the specification and practice of the invention disclosed herein. It is intended that the specification and examples be considered as exemplary only, with the true scope and spirit of the invention being indicated by the claims. Any references set forth above are hereby incorporated by reference herein, and no admission is intended as to these publications constituting prior art.

We claim:

1. A method of attenuating the effect of pathogenic bacterial enterotoxins, comprising obtaining a pharmaceutical composition comprising cadaverine and a pharmaceutical carrier, and administering to a host an amount of the pharmaceutical composition effective to attenuate the effect of pathogenic bacterial enterotoxins.

2. The method of claim 1, wherein the host is a human.

3. The method of claim 1, wherein the pathogenic bacterial enterotoxins are produced by a Shigella spp.

4. The method of claim 1, wherein the pathogenic bacterial enterotoxins are produced by one or more of Shigella spp., enteropathogenic E. coil, enterohemorrhagic E. coil, enterotoxigenic E. coil, enteroaggregative E. coil, uropathogenic E. coil, meningitis-causing E. coil, Yersinia pestis, Yersinia pseudotuberculosis, Yersinia enterocolitica, Mycobacterium bovis, Listeria monocytogenes, Vibrio cholerae, Streptococcus pyogenes, Campylobacter jejuni, or Bacteroides fragilis.

5. The method of claim 1, wherein the pharmaceutical composition is also in an amount effective to attenuate transepithelial migration of polymorphonuclear leukocytes.

* * * * *

UNITED STATES PATENT AND TRADEMARK OFFICE
CERTIFICATE OF CORRECTION

PATENT NO.     : 6,780,414 B2  
DATED          : August 24, 2004  
INVENTOR(S)    : Anthony Maurelli et al.

It is certified that error appears in the above-identified patent and that said Letters Patent is hereby corrected as shown below:

Title page,  
Item [*] Notice, delete "This patent is subject to a terminal disclaimer."

Column 28,  
Lines 56 and 57, "*E. coil*," (both occurrences) should read -- *E. coli*, --.  
Line 58, "*E. coil*," (first occurrence) should read -- *E. coli*, --;  
Line 58, "meningitis-causing *E. coil*," should read -- meningitis-causing *E. coli* K-1, --.

Signed and Sealed this

Fifth Day of April, 2005

JON W. DUDAS  
*Director of the United States Patent and Trademark Office*